(12) United States Patent
Badie et al.

(10) Patent No.: US 9,675,805 B2
(45) Date of Patent: Jun. 13, 2017

(54) METHOD AND SYSTEM FOR LOCALIZING LEFT VENTRICULAR CONDUCTION NON-UNIFORMITY

(71) Applicant: Pacesetter, Inc., Sunnyvale, CA (US)

(72) Inventors: Nima Badie, Mountain View, CA (US); Fujian Qu, San Jose, CA (US); Kyungmoo Ryu, Palmdale, CA (US); Luke C. McSpadden, Los Angeles, CA (US); Caroline Jordan, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 6 days.

(21) Appl. No.: 14/805,883

(22) Filed: Jul. 22, 2015

(65) Prior Publication Data

US 2017/0021176 A1 Jan. 26, 2017

(51) Int. Cl.
*A61N 1/36* (2006.01)
*A61N 1/368* (2006.01)
*A61N 1/37* (2006.01)

(52) U.S. Cl.
CPC ......... *A61N 1/3686* (2013.01); *A61N 1/3684* (2013.01); *A61N 1/371* (2013.01)

(58) Field of Classification Search
CPC ............................ A61N 1/3684; A61N 1/3686
See application file for complete search history.

(56) References Cited

U.S. PATENT DOCUMENTS

| | | | |
|---|---|---|---|
| 2011/0098770 A1* | 4/2011 | Ryu | A61N 1/3627 607/25 |
| 2015/0134023 A1* | 5/2015 | McSpadden | A61B 5/0452 607/17 |

* cited by examiner

*Primary Examiner* — Eric D. Bertram
(74) *Attorney, Agent, or Firm* — Theresa A. Raymer

(57) ABSTRACT

Methods, devices and systems are provided for selecting one or more left ventricular multi-electrode pacing site(s). The methods, devices and systems measure arrival times of LV activation events for corresponding LV sensing sites, where the arrival times each correspond to a conduction time from an intrinsic ventricular event or delivery of a pacing pulse until sensing of the corresponding LV activation event. Site-to-site (STS) relative delays are calculated as differences between the arrival times associated with adjacent LV sensing sites. The STS relative delays represent STS arrival delays for corresponding combinations of the adjacent LV sensing sites. An LV electrode combination is identified that is associated with at least one of the STS relative delays that satisfy selection criteria, where the LV electrode combination corresponds to a target tissue region exhibiting a select degree of non-uniformity. The LV electrode combination is designated as a first LVEC pacing site from which to deliver LV pacing pulses.

20 Claims, 8 Drawing Sheets

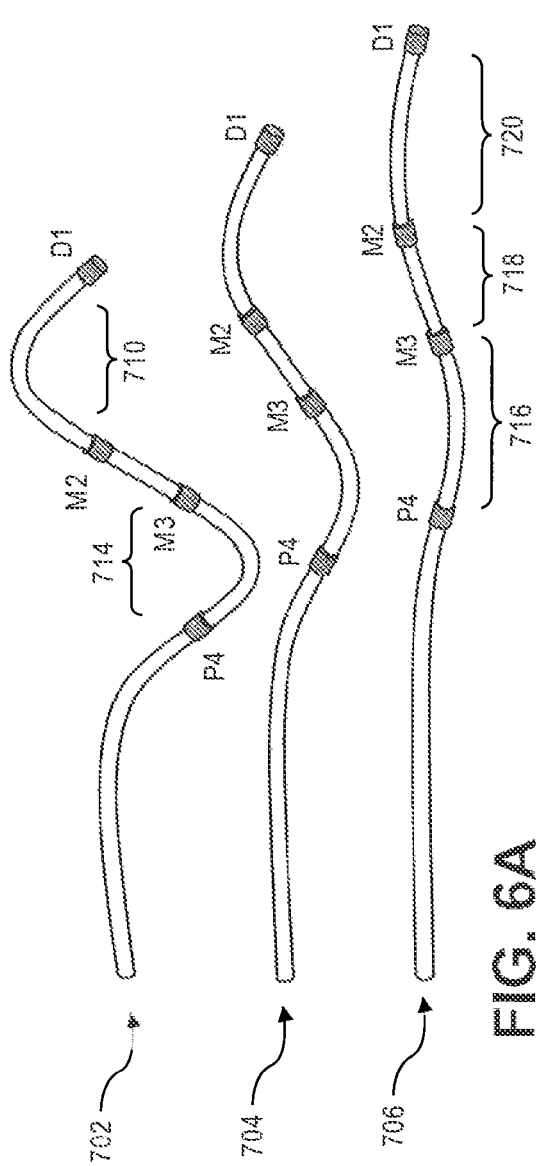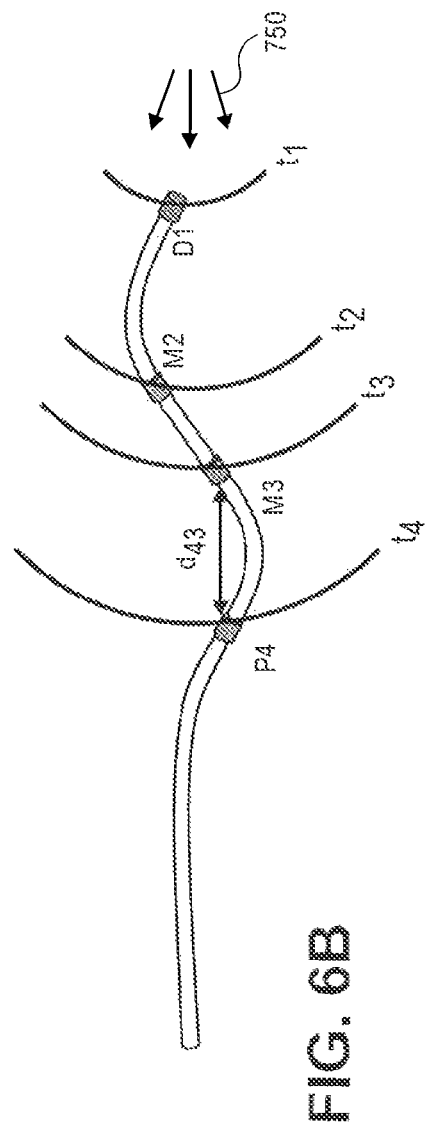
FIG. 6A
FIG. 6B

METHOD AND SYSTEM FOR LOCALIZING LEFT VENTRICULAR CONDUCTION NON-UNIFORMITY

BACKGROUND

One or more embodiments of the subject matter herein relate to quantifying and localizing left ventricular (LV) electrical conduction non-uniformity based on sensed events along a multipolar LV lead.

Implantable stimulation devices or cardiac pacemakers are a class of cardiac rhythm management devices that provide electrical stimulation in the form of pacing pulses to selected chambers of the heart. As the term is used herein, a pacemaker is any cardiac rhythm management device with a pacing functionality regardless of any additional functions it may perform, such as cardioversion/defibrillation.

A pacemaker is comprised of two major components, a pulse generator and a lead. The pulse generator generates the pacing stimulation pulses and includes the electronic circuitry and the power cell or battery. The lead, or leads, is implanted within the heart and has electrodes which electrically couple the pacemaker to the desired heart chamber(s). A lead may provide both unipolar and bipolar pacing and/or sensing configurations. In the unipolar configuration, the pacing pulses are applied (or responses are sensed) between an electrode carried by the lead and a case of the pulse generator or a coil electrode of another lead within the heart. In the bipolar configuration, the pacing pulses are applied (or responses are sensed) between a pair of electrodes carried by the same lead. Pacemakers are also described as single-chamber or dual-chamber systems. A single-chamber system stimulates and senses in one chamber of the heart (an atrium or a ventricle). A dual-chamber system stimulates and/or senses in at least one atrial chamber and at least one ventricular chamber. Recently, pacing systems have been introduced that stimulate multiple sites in the same chamber, termed multisite stimulation systems or multi-purpose pacing systems.

When the patient's own intrinsic rhythm fails, pacemakers can deliver pacing pulses to a heart chamber to induce a depolarization of that chamber, which is followed by a mechanical contraction of that chamber. Pacemakers further include sensing circuits that sense cardiac activity for the detection of intrinsic cardiac events such as intrinsic atrial depolarizations (detectable as P waves) and intrinsic ventricular depolarizations (detectable as R waves). By monitoring cardiac activity, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart. This therapy is referred to as cardiac resynchronization therapy (CRT).

Recently, multi-point pacing (MPP) technology has enabled pacing at left ventricular (LV) sites to improve synchrony in cardiac resynchronization therapy (CRT) patients. Improvements in synchrony and improved hemodynamic response have been shown to depend on the MPP configuration. In the past, MPP configurations have been selected based on reducing pacing capture thresholds, avoiding atrial and phrenic nerve capture, and maximizing anatomical distance between two LV pacing sites. However, addressing the non-uniformity of electrical conduction at the four LV electrodes, due to local dyssynchrony in the surrounding heart tissue, may enhance the benefit of MPP. A need remains for improved methods and systems to identify preferred MPP configurations.

SUMMARY

In accordance with embodiments herein, methods and systems are provided that quantify and localize non-uniformity of LV electrical conduction and that suppress the non-uniformity through control of the MPP configuration. When properly managed, MPP therapy may provide greater systolic blood pressure elevation than other pacing therapies, such as bi-ventricular pacing therapy that uses a single LV pacing site, in patients who experience non-uniformity of LV electrical activation.

In accordance with embodiments herein, a method is provided for selecting a left ventricular multi-electrode (LVME) pacing site for an implantable medical device (IMD) equipped for cardiac stimulus pacing using a multi-pole left ventricular (LV) lead. The method comprises sensing LV activation events at multiple LV sensing sites, where the activation events are generated in response to intrinsic ventricular electrical conduction or delivery of a pacing pulse in the ventricles. The method further comprises measuring arrival times of the LV activation events for the corresponding LV sensing sites, where the arrival times each correspond to a conduction time from the atrial activation event or delivery of the pacing pulse in the ventricles until sensing of the corresponding LV activation event. The method further calculates site-to-site (STS) relative delays as differences between the arrival times associated with adjacent LV sensing sites. The STS relative delays represent STS arrival delays for corresponding combinations of the adjacent LV sensing sites. The method identifies an LV electrode combination (LVEC) associated with at least one of the STS relative delays that satisfies selection criteria, where the LV electrode combination corresponds to a target tissue region exhibiting a select degree of non-uniformity as indicated by the corresponding STS relative delay. The method designates the LV electrode combination as a first LVEC pacing site from which to deliver LV pacing pulses using the implantable medical device. In accordance with embodiments herein, the first LVEC pacing site corresponds to a combination of individual electrode pacing vectors that extend between an anode and two or more cathode electrodes within the LV electrode combination. The LV electrodes at the first LVEC pacing site serve as cathodes for two separate pacing vectors extending from the corresponding LV cathode electrode and a separate anode, but where the two separate pacing vectors are paced near-simultaneously or with a short delay there between. The anode electrode may correspond to an RA electrode, an RV electrode, an LA electrode and/or CAN electrode. As one example, first and second LV electrodes may be configured as cathodes within first and second pacing vectors for MPP, wherein the first and second electrodes are associated with a largest STS relative delay.

Optionally, the selection criteria may be based in part on a relation between the STS relative delays and a maximum arrival time difference among the LV electrodes on the lead. The maximum arrival time difference represents the difference between an earliest arrival time sensed by the LV electrodes and a latest arrival time sensed by the LV electrodes. Optionally, the method may deliver a pacing sequence from the LV electrode combination designated for the first LVEC pacing site, wherein a first LVEC pacing pulse in the pacing sequence is delivered from the LV electrode combination.

Optionally, the LV electrode combination may include an adjacent pair of the LV electrodes, where the method utilizes the adjacent pair of LV electrodes as cathodes when delivering the LV pacing pulses. Optionally, the designating operation may include designating adjacent at least first and second LV electrodes as cathodes to simultaneously deliver at least a first LVEC pacing pulse.

In accordance with embodiments herein, the calculating operation further comprises quantifying a spatiotemporal non-uniformity as the select degree of non-uniformity based on local conduction velocity. Optionally, the calculating operation may further comprise calculating a local conduction velocity based on the STS relative delays and STS relative distances between the LV electrodes corresponding to the adjacent LV sensing sites.

In accordance with embodiments herein, the method configures the first LVEC pacing site to be a cathode within a pacing vector, where the pacing vector extends between the first LVEC pacing site and at least one of a CAN electrode, a right atrial electrode, and a right ventricular electrode. The first LVEC pacing site may correspond to one of a D1, M2, M3, or P4 electrode provided on the multi-pole LV lead. Optionally, the method may further comprise determining distances between adjacent LV electrodes on the multi-pole LV lead, while the identifying operation identifies the LV electrode combination that satisfies the selection criteria based in part on the distances between adjacent LV electrodes.

In accordance with embodiments herein, an implantable medical device is provided for cardiac stimulus pacing using a multi-pole left ventricular (LV) lead. The device comprises a sensor configured to sense LV activation events at multiple LV sensing sites, where the activation events are generated in response to an intrinsic ventricular event or a delivery of a pacing pulse. The device further comprises an arrival measurement (AM) module configured to measure arrival times of the LV activation events for the corresponding LV sensing sites, wherein the arrival times each correspond to a conduction time from delivery of the pacing pulse until sensing of the corresponding LV activation event. The device further comprises a delay calculation (DC) module configured to calculate site-to-site (STS) relative delays as differences between the arrival times associated with adjacent LV sensing sites, the STS relative delays representing STS arrival delays for corresponding combinations of the adjacent LV sensing sites. The device further comprises a site designation (SD) module configured to identifying an LV electrode combination associated with at least one of the STS relative delays that satisfies selection criteria. The LV electrode combination corresponds to a target tissue region exhibiting a select degree of non-uniformity as indicated by the corresponding STS relative delay. The SD module designates the LV electrode combination as a first LVEC pacing site from which to deliver LV pacing pulses using the implantable medical device.

Optionally, the device further comprises a pulse generator to deliver a pacing sequence from the LV electrode combination designated for the first LVEC pacing site, where the pulse generator to deliver a first LV pacing pulse in the pacing sequence from the LV electrode combination. Optionally, the LV electrode combination includes an adjacent pair of LV electrodes. The device further comprises a pulse generator coupled to a switch that sets the adjacent pair of LV electrodes as cathodes when delivering the LV pacing pulses.

Optionally, the device further comprises a pulse generator and switch that are controlled by the site designation module to designate adjacent at least first and second LV electrodes as cathodes to simultaneously deliver at least a first pacing pulse. In accordance with some embodiments, the device comprises a microcontroller and memory storing programmable instructions, where the microcontroller executes the programmable instructions to implement the DC module to calculate the relative STS delays. In accordance with an embodiment, the device comprises a microcontroller and memory storing programmable instructions, where the microcontroller executes the programmable instructions to implement the site designation module to identify the LV electrode combination associated with one of the STS relative delays and to designate the LV electrode combination as the first LVEC pacing site. In accordance with some embodiments, the AM module includes timer electronic circuitry to measure the arrival times, and the DC module comprising electronic circuitry to calculate the STS relative delays.

In accordance with embodiments herein, the system is provided for cardiac stimulus pacing using a multi-pole left ventricular (LV) lead. The system comprises memory to store arrival times of LV activation events for corresponding LV sensing sites, the LV activation events occurring at multiple LV sensing sites, wherein the activation events are generated in response to a delivery of a pacing pulse and wherein the arrival times each correspond to a conduction time from delivery of a pacing pulse until sensing of the corresponding LV activation event. The system comprises one or more processors coupled to the memory, wherein the memory further stores program instructions. The program instructions are executable by the one or more processors to calculate site-to-site (STS) relative delays as differences between the arrival times associated with adjacent LV sensing sites, the STS relative delays representing STS arrival delays for corresponding combinations of the adjacent LV sensing sites, to identify an LV electrode combination associated with at least one of the STS relative delays that satisfies a selection criteria, the LV electrode combination corresponding to a target tissue region exhibiting a select degree of non-uniformity as indicated by the corresponding STS relative delay; and to designate the LV electrode combination as a first LVEC pacing site from which to deliver LV pacing pulses using the implantable medical device.

BRIEF DESCRIPTION OF THE DRAWINGS

FIG. 6A illustrates examples of STS relative spacings for a distal portion of an LV lead that may be shaped in accordance with embodiments herein.

FIG. 6B illustrates an example of calculations of STS conduction velocities between various LV electrode combinations as a waveform propagates from the distal end to the proximal end of the LV lead.

DETAILED DESCRIPTION

Figure 1:
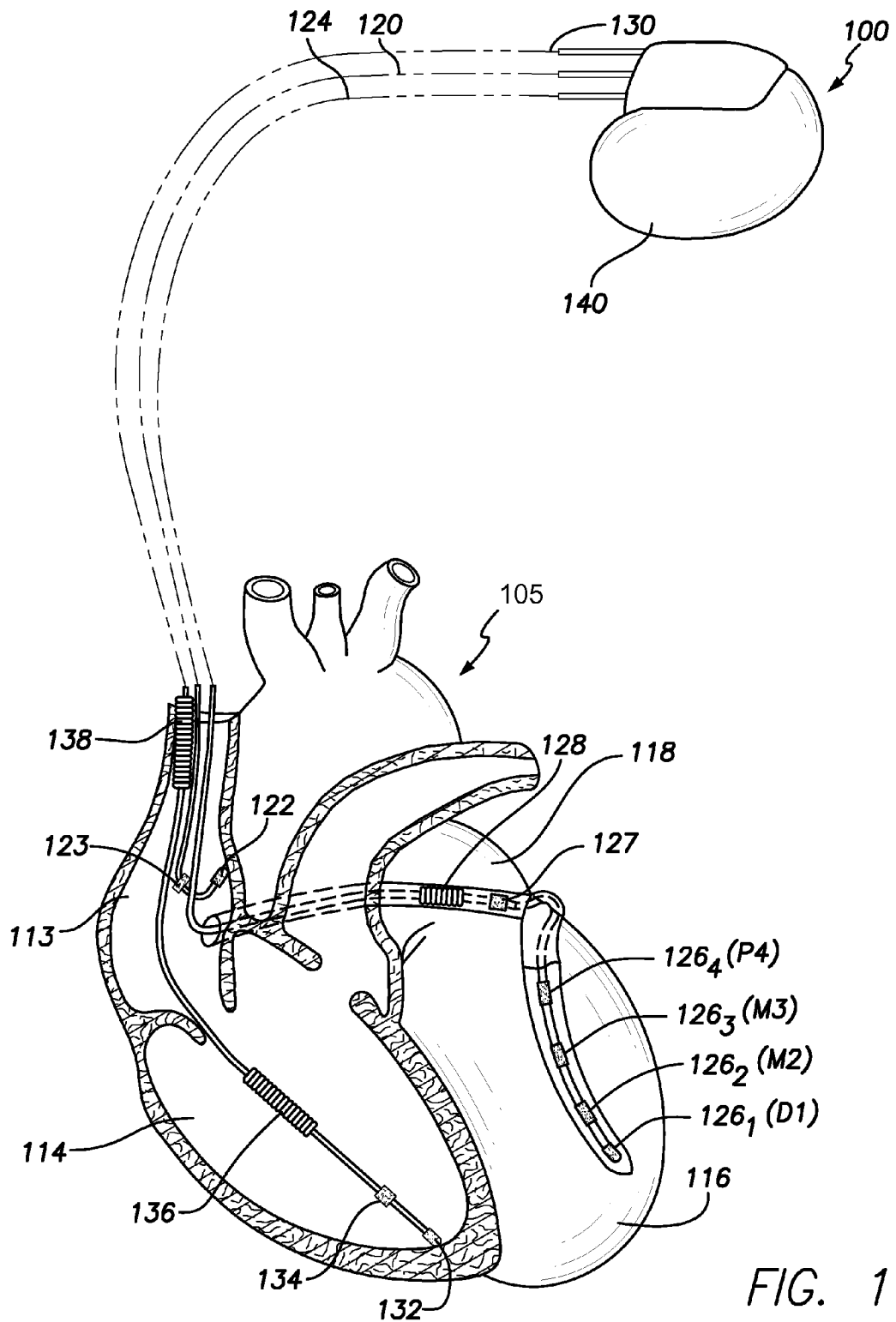
FIG. 1 illustrates an implantable medical device (IMD) in electrical communication with multiple leads implanted into a patient's heart for delivering multi-chamber stimulation and sensing cardiac activity according to an embodiment.

The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware and circuitry. Thus, for example, one or more of the functional blocks (e.g., processors or memories) may be implemented in a single piece of hardware (e.g., a general purpose signal processor, microcontroller, random access memory, hard disk, and/or the like). Similarly, the programs may be standalone programs, may be incorporated as subroutines in an operating system, may be functions in an installed imaging software package, and the like. Furthermore, to the extent that the figures illustrate flow diagrams of processes of various embodiments, the operations may be described by adding, rearranging, combining, or omitting the illustrated operations without departing from the scope of the processes as described herein. It should be understood that the various embodiments are not limited to the arrangements and instrumentality shown in the drawings.

The block diagrams of embodiments herein illustrate various blocks labeled "module". It is to be understood that the modules represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard-wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

As used herein, an element or step recited in the singular and proceeded with the word "a" or "an" should be understood as not excluding plural of said elements or steps, unless such exclusion is explicitly stated. Furthermore, references to "an embodiment" or "one embodiment" of the inventive subject matter are not intended to be interpreted as excluding the existence of additional embodiments that also incorporate the recited features. Moreover, unless explicitly stated to the contrary, embodiments "including," "comprising," or "having" (and various forms thereof) an element or a plurality of elements having a particular property may include additional such elements not having that property.

One or more embodiments generally relate to implantable medical devices and systems such as pacemakers and implantable cardioverter-defibrillators (ICDs). One or more embodiments relate, in particular, to such devices and systems that include a multi-pole LV lead capable of pacing from one or more electrodes along the multi-pole lead, and methods for use therewith.

New multipolar left ventricular (LV) leads have been developed for implantable medical devices (IMDs) that include multiple electrodes for placement in the LV chamber. For example, St. Jude Medical, Inc. (headquartered in St. Paul, Minn.) has developed the Quartet™ LV pacing lead, which includes four pacing electrodes on the LV lead.

In accordance with embodiments herein, methods and systems provide synchrony through a quantification process that is based on the timing of local, inter-electrode electrical conduction. The quantification process measures arrival or activation times (e.g. at an IMD) as an electrical wavefront propagates past each of a number of electrodes (e.g. 4) located along a multipolar left ventricular (LV) lead. The arrival or activation times are compared to calculate relative delays between sensing sites, also referred to as site-to-site (STS) relative delay. The STS relative delay between each neighboring pair of LV electrodes is used to quantify the non-uniformity of conduction in the surrounding local tissue associated with each corresponding electrode pair. Conduction non-uniformities of local tissue may be attributed to focal ischemic lesions or other causes. The distinct regions associated with each of the LV electrodes exhibit different degrees of non-uniformity. The local region exhibiting a highest degree of non-uniformity may be identified using the inter-electrode activation time delays. In some embodiments herein, the electrode pair associated with the local region exhibiting the highest degree of non-uniformity is chosen as a combined LVEC pacing site such that poorly conducting tissue is directly stimulated by MPP therapy delivered at the neighboring electrode cathode pair, thereby creating a more uniform wavefront propagation with less conduction block and/or delay. By choosing the electrode pair exhibiting the highest degree of non-uniformity for a combined electrode cathode pair, the processes described herein avoid designating pacing vectors that are detached from the local tissue having poor conduction.

Various techniques are described herein for identifying the electrode combination (e.g. pair) associated with a local region exhibiting a select (e.g. highest) degree of non-uniformity. In accordance with one technique, inter-electrode distances are assumed to be roughly equivalent such that non-uniformity calculations are based primarily (e.g. solely) on time, namely on the STS relative delays. Temporal non-uniformity may be quantified by calculating the neighboring electrode activation time difference (STS relative delays) as a percentage of a maximum activation time difference or overall activation time interval. For example, the maximum activation time difference may be derived from the delay between an earliest sensed electrical activation and a latest sensed electrical activation sensed by the collection of LV electrodes on the LV lead. There is a high degree of likelihood that neighboring LV electrodes that are associated with a select amount of delay (e.g. the largest delay) will encompass local tissue with a desired (e.g. highest) degree of electrical dysfunction.

In accordance with other techniques herein, inter-electrode distances may be accounted for such that non-uniformity calculations are based on time and distance. For example, once an LV lead is implanted, at least basic information may be collected or assumed regarding a trajectory and shape of a distal portion of the LV lead. When information is known regarding the trajectory and shape of the distal portion of the LV lead, the distance between each pair of adjacent electrodes may be estimated or measured to determine a site-to-site relative spacing or distance. The STS relative delays are calculated as noted above, but now combined with the STS relative distance or spacing in order to calculate conduction velocity as an indication of spatial-temporal non-uniformity. For example, mean conduction velocity for local tissue regions between each neighboring pair of LV electrodes may be calculated as the distance between the electrodes (STS relative distance or spacing) divided by the difference in the respective sensed activation times (STS relative delay). The electrode pair exhibiting the slowest conduction velocity is assumed to be associated with local tissue having a select degree of electrical dysfunction (e.g. highest).

The activation time corresponds to the point in time when an LV electrode senses an activation event responsive to a pacing pulse along a sensing vector. In one or more embodiments described herein, an IMD with a multipolar LV lead is used to measure inter-electrode LV activation times between adjacent pairs of LV electrodes spaced along the multipolar LV lead after RV pacing. The measured inter-electrode LV activation times are used to identify and automatically program/reprogram a preferred LV electrode combination (LVEC) pacing site that may result in improved acute hemodynamic response. As used herein, the term "first LVEC pacing site" corresponds to a combination of individual electrode pacing sites associated with the LV electrodes within the LV electrode combination. In accordance with an embodiment, two or more cathode electrodes within the LV electrode combination may be used to deliver separate pacing pulses successively very close in time (e.g., "nearly simultaneous"). When the two or more cathode electrodes are used to deliver successive "nearly simultaneous" pacing pulses, the first LVEC pacing site is associated with a combination of pacing vectors that extend between an anode and the corresponding one of the two or more cathode electrodes. In accordance with another embodiment, two or more cathode electrodes within the LV electrode combination may be used simultaneously to deliver a pacing pulse. When the two or more cathode electrodes are used to simultaneously deliver a pacing pulse, the first LVEC pacing site is associated with a "virtual" vector that extends between an anode (remote from the LV) and a virtual point between the two or more cathode electrodes. The anode electrode may correspond to an RA electrode, an RV electrode, an LA electrode and/or CAN electrode. As one example, first and second LV electrodes may be configured as cathodes within first and second pacing vectors for MPP, wherein the first and second electrodes are associated with a largest STS relative delay. The process may be performed at least in part by an algorithm within the IMD or an external programmer. Conduction delay measurements refer to the conduction time from delivery of the pacing pulse until sensing of the corresponding LV activation event at various LV sensing sites in response to the pacing pulse, and may also be referred to herein as "arrival time." The LV electrodes at the LVEC pacing site are used as pacing cathodes to deliver pacing pulses to the heart.

Figure 2:
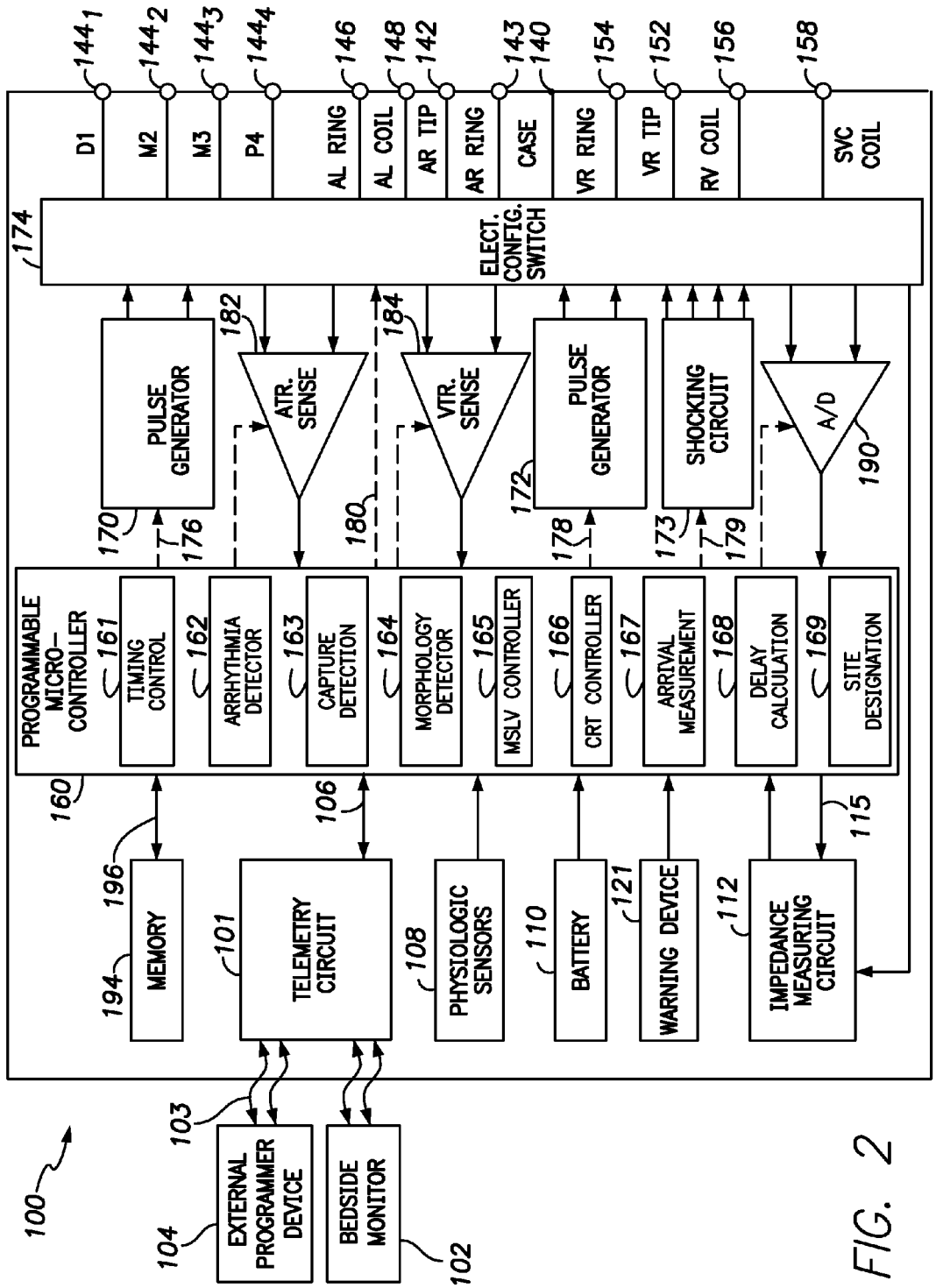
FIG. 2 illustrates a simplified block diagram of internal components of the IMD in accordance with embodiments herein.

In view of the above, FIGS. 1 and 2 illustrate an IMD equipped for cardiac stimulus pacing using a multi-pole LV lead, in which embodiments described herein may be implemented.

FIG. 1 illustrates an implantable medical device (IMD) 100 in electrical communication with multiple leads implanted into a patient's heart 105 for delivering multi-chamber stimulation and sensing cardiac activity according to an embodiment. The IMD 100 may be a dual-chamber stimulation device, including a IMD, capable of treating both fast and slow arrhythmias with stimulation therapy, including cardioversion, defibrillation, and pacing stimulation, including CRT. Optionally, the IMD 100 may be configured for multi-site left ventricular (MSLV) pacing, which provides pacing pulses at more than one site within the LV chamber each pacing cycle. The IMD 100 may be referred to herein as IMD 100. To provide atrial chamber pacing stimulation and sensing, IMD 100 is shown in electrical communication with a heart 105 by way of a left atrial (LA) lead 120 having an atrial tip electrode 122 and an atrial ring electrode 123 implanted in the atrial appendage 113. IMD 100 is also in electrical communication with the heart 105 by way of a right ventricular (RV) lead 130 having, in this embodiment, a ventricular tip electrode 132, an RV ring electrode 134, an RV coil electrode 136, and a superior vena cava (SVC) coil electrode 138. The RV lead 130 is transvenously inserted into the heart 105 so as to place the RV coil electrode 136 in the RV apex, and the SVC coil electrode 138 in the superior vena cava. Accordingly, the RV lead 130 is capable of receiving cardiac signals and delivering stimulation in the form of pacing and shock therapy to the right ventricle 114 (also referred to as the RV chamber).

To sense left atrial and ventricular cardiac signals and to provide left ventricle 116 (e.g., left chamber) pacing therapy, IMD 100 is coupled to a multi-pole LV lead 124 designed for placement in the "CS region." As used herein, the phrase "CS region" refers to the venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus. In an embodiment, an LV lead 124 is designed to receive atrial and ventricular cardiac signals and to deliver left ventricular pacing therapy using a set of multiple LV electrodes 126 that includes electrodes $126_1$, $126_2$, $126_3$, and $126_4$ (thereby providing a multipolar or multi-pole lead). The LV lead 124 also may deliver left atrial pacing therapy using at least an LA ring electrode 127 and shocking therapy using at least an LA coil electrode 128. In alternate embodiments, the LV lead 124 includes the LV electrodes $126_1$, $126_2$, $126_3$, and $126_4$, but does not include the LA electrodes 127 and 128. The LV lead 124 may be, for example, the Quartet™ LV pacing lead developed by St. Jude Medical Inc. (headquartered in St. Paul, Minn.), which includes four pacing electrodes on the LV lead. Although three leads 120, 124, and 130 are shown in FIG. 1, fewer or additional leads with various numbers of pacing, sensing, and/or shocking electrodes may optionally be used. For example, the LV lead 124 may have more or less than four LV electrodes 126.

When selecting a target venous branch for the LV lead 124, several factors may be taken into account. For example, it may be desirable to maximize the LV mass that may be captured by the LV lead 124. Accordingly, to maximize LV mass exposure, certain venous branches may be preferred for positioning the LV lead 124. Further, a diameter and trajectory of the venous branch is also considered to ensure that the venous branch will support chronic stability of an LV lead 124. Passive fixation of the LV lead 124 may be established through the anatomy of the host venous branch which causes the LV lead 124 to extend the distal portion thereof in a manner that differs from the LV lead's preformed shape. Optionally, additional factors to be considered when placing the LV lead 124 may include reducing myocardial capture thresholds, avoiding atrial and phrenic nerve stimulation and the like. After the LV lead 124 is positioned, the LV pacing vectors may be selected. LV pacing vectors have been shown to have influence on MPP efficacy. Electrical heterogeneity of the tissue local to the LV electrodes (e.g. local dyssynchrony) influences MPP efficacy. As explained herein, improved methods and systems quantified and localize the dyssynchrony and based therein, set the LVEC pacing site(s).

The LV electrode $126_1$ is shown as being the most "distal" LV electrode with reference to how far the electrode is from the left atrium 118. The LV electrode $126_4$ is shown as being the most "proximal" LV electrode 126 to the left atrium 118. The LV electrodes $126_2$ and $126_3$ are shown as being "middle" LV electrodes, between the distal and proximal LV electrodes $126_1$ and $126_4$, respectively. Accordingly, so as to more aptly describe their relative locations, the LV electrodes $126_1$, $126_2$, $126_3$, and $126_4$ may be referred to respectively as electrodes D1, M2, M3, and P4 (where "D" stands for "distal", "M" stands for "middle", and "P" stands from "proximal", and the numbers are arranged from most distal to most proximal, as shown in FIG. 1). Optionally, more or fewer LV electrodes may be provided on the lead 124 than the four LV electrodes D1, M2, M3, and P4.

The LV electrodes 126 are configured such that each electrode may be utilized to deliver pacing pulses and/or sense pacing pulses (e.g., monitor the response of the LV tissue to a pacing pulse). In a pacing vector or a sensing vector, each LV electrode 126 may be controlled to function as a cathode (negative electrode). Pacing pulses may be directionally provided between electrodes to define a pacing vector. As explained herein, combinations of LV electrodes 126 are paired with one another to operate as a common virtual electrode, such as a common virtual cathode, when delivering pacing therapies. In a pacing vector, a generated pulse is applied to the surrounding myocardial tissue through the cathode. The electrodes that define the pacing vectors may be electrodes in the heart 105 or located externally to the heart 105 (e.g., on a housing/case device 140). For example, the housing/case 140 may be referred to as the CAN 140 and function as an anode in unipolar pacing and/or sensing vectors. The LV electrodes 126 may be used to provide various different vectors. Some of the vectors are intraventricular LV vectors (e.g., vectors between two of the LV electrodes 126), while other vectors are interventricular vectors (e.g. vectors between an LV electrode 126 and the RV coil 136 or another electrode remote from the left ventricle 116). Below is a list of exemplary bipolar sensing vectors with LV cathodes that may be used for sensing using the LV electrodes D1, M2, M3, and P4 and the RV coil 136. In the following list, the electrode to the left of the arrow is assumed to be the cathode, and the electrode to the right of the arrow is assumed to be the anode.

D1→RV coil
M2→RV coil
M3→RV coil
P4→RV coil
D1→M2
D1→P4
M2→P4
M3→M2
M3→P4
P4→M2

It is recognized that various other types of leads and IMDs may be used with various other types of electrodes and combinations of electrodes. The foregoing electrode types/combinations are provided as non-limiting examples. Further, it is recognized that utilizing an RV coil electrode as an anode is merely one example. Various other electrodes may be configured as the anode electrode. Below is a list of exemplary bipolar pacing vectors with LV cathodes that may be used for pacing using the LV electrodes D1, M2, M3, and P4 and the RV coil 136. In the following list, the electrodes to the left of the arrow are assumed to be cathodes, and the electrode to the right of the arrow is assumed to be the anode.

D1→RV coil (or CAN)+M2→RV coil (or CAN)
M2→RV coil (or CAN)+M3→RV coil (or CAN)
M3→RV coil (or CAN)+M4→RV coil (or CAN)
M2→RV coil (or CAN)+M3→RV coil (or CAN)+P4→RV coil (or CAN)
D1→RV coil (or CAN)+M2→RV coil (or CAN)+M3→RV coil (or CAN)

It is noted that the preceding list is only a subset of the available pacing and sensing vectors for use with the IMD 100. Further, when delivering a series of pacing pulses, one of the above LVEC pacing vectors is used for at least the first pacing pulse in the series. Other pacing vectors may be used for subsequent pulses in the series of pacing pulses. Furthermore, additional pacing pulses may be generated in other chambers of the heart, such as the right ventricle.

FIG. 2 illustrates a simplified block diagram of internal components of the IMD 100 (e.g., IMD) according to an embodiment. While a particular IMD 100 is shown, it is for illustration purposes only. One of skill in the art could readily duplicate, eliminate, or disable the appropriate circuitry in any desired combination to provide a device capable of treating the appropriate chamber(s) with cardioversion, defibrillation, and pacing stimulation. The housing/CAN 140 for IMD 100, shown schematically in FIG. 2 may be programmably selected to act as the anode for at least some unipolar modes. The CAN 140 may further be used as a return electrode alone or in combination with one or more of the coil electrodes 128, 136, and 138 (all shown in FIG. 1) for shocking purposes.

The IMD 100 further includes a connector (not shown) having a plurality of terminals, 142, 143, $144_1$-$144_4$, 146, 148, 152, 154, 156, and 158 (shown schematically and, for convenience, with the names of the electrodes to which they are connected). As such, to achieve right atrial (RA) sensing and pacing, the connector includes at least an RA tip terminal ($A_R$ TIP) 142 adapted for connection to the atrial tip electrode 122 (shown in FIG. 1) and an RA ring ($A_R$ RING) electrode 143 adapted for connection to the RA ring electrode 123 (shown in FIG. 1). To achieve left chamber sensing, pacing, and shocking, the connector includes an LV tip terminal $144_1$ adapted for connection to the D1 electrode and additional LV electrode terminals $144_2$, $144_3$, and $144_4$ adapted for connection to the M2, M3, and P4 electrodes, respectively, of the quadripolar LV lead 124 (shown in FIG. 1). The connector also includes an LA ring terminal ($A_L$ RING) 146 and an LA shocking terminal ($A_L$ COIL) 148, which are adapted for connection to the LA ring electrode 127 (shown in FIG. 1) and the LA coil electrode 128 (shown in FIG. 1), respectively. To support right chamber sensing, pacing, and shocking, the connector further includes an RV tip terminal ($V_R$ TIP) 152, an RV ring terminal ($V_R$ RING) 154, an RV coil terminal (RV COIL) 156, and an SVC coil terminal (SVC COIL) 158, which are adapted for connection to the RV tip electrode 132, the RV ring electrode 134, the RV coil electrode 136, and the SVC coil electrode 138 (all four electrodes shown in FIG. 1), respectively.

At the core of the IMD 100 is a programmable microcontroller 160, which controls the various modes of stimulation therapy. The microcontroller 160 (also referred to herein as a control unit or controller) includes a microprocessor or equivalent control circuitry, designed specifically for controlling the delivery of stimulation therapy. The microcontroller 160 may further include RAM or ROM memory, logic and timing circuitry, state machine circuitry, and/or I/O circuitry. The microcontroller 160 includes the ability to process or monitor input signals (data) as controlled by a program code stored in a designated block of memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes. For example, the cardiac data sets may include DI data, SI data, LTV information, STV information, IEGM data, pressure data, heart sound data, and the like.

A pulse generator 170 and a pulse generator 172 are configured to generate and deliver a pacing pulse from at least one RV or RA pacing site, such as at one or more pacing sites along the RA lead 120, the RV lead 130, and/or the LV lead 124 (all three leads shown in FIG. 1). For example, the pulse generator 170 generates pulses for delivery by the RA lead 120 and/or RV lead 130, while the pulse generator 172 generates pulses for delivery by the LV lead 124. The pacing pulses are routed from the pulse generators 170, 172 to selected electrodes within the leads 120, 124, 130 through an electrode configuration switch 174. It is understood that in order to provide stimulation therapy in each of the four chambers of the heart, the pulse generators 170 and 172, may include dedicated, independent pulse generators, multiplexed pulse generators, or shared pulse generators. The pulse generators 170, 172 are controlled by the microcontroller 160 via appropriate control signals 176, 178, respectively, to trigger or inhibit the stimulation pulses, including the timing and output of the pulses.

The electrode configuration switch 174 may include a plurality of switches for connecting the desired electrodes to the appropriate I/O circuits, thereby providing complete electrode programmability. Accordingly, the switch 174, in response to a control signal 180 from the microcontroller 160, controls the polarity of the stimulation pulses (e.g., unipolar, bipolar, combipolar, etc.) by selectively actuating the appropriate combination of switches (not shown) as is known in the art. The switch 174 also switches among the various LV electrodes 126 to select the channels (e.g., vectors) to deliver and/or sense one or more of the pacing pulses. As explained herein, the switch 174 couples multiple LV electrode terminals $144_1$-$144_4$ correspond to cathodes when connected to the pulse generator 172.

Atrial sensors or sensing circuits 182 and ventricular sensors or sensing circuits 184 may also be selectively coupled to the RA lead 120, the LV lead 124, and/or the RV lead 130 (all three leads shown in FIG. 1) through the switch 174. The atrial and ventricular sensors 182 and 184 have the ability to detect the presence of cardiac activity in each of the four chambers of the heart 105 (shown in FIG. 1). For example, the ventricular sensor 184 is configured to sense LV activation events at multiple LV sensing sites, where the activation events are generated in response to a pacing pulse or an intrinsic event. In an embodiment, the ventricular sensor 184 senses along at least four sensing vectors, each sensing vector utilizing a sensing electrode in the left ventricle.

The atrial sensing circuits 182 and ventricular sensing circuits 184 may include dedicated sense amplifiers, multiplexed amplifiers, or shared amplifiers. The switch 174 determines the "sensing polarity" or sensing vector of the cardiac signal by selectively opening and/or closing the appropriate switches, as is known in the art. In this way, a clinician may program the sensing polarity independent of the stimulation polarity. The outputs of the atrial and ventricular sensing circuits 182 and 184 are connected to the microcontroller 160. The outputs, in turn, are able to trigger or inhibit the atrial and ventricular pulse generators 170 and 172, respectively, in a demand fashion in response to the absence or presence of cardiac activity in the appropriate chambers of the heart 105.

Cardiac signals are also applied to the inputs of an analog-to-digital (A/D) data acquisition system 190. The A/D data acquisition system 190 is configured to acquire intracardiac electrogram (IEGM) signals, convert the raw analog data into a digital signal, and store the digital signals for later processing and/or telemetric transmission. The telemetric transmission may be to an external programmer 104, a bedside monitor, and/or a personal advisory module (PAM) 102. The data acquisition system 190 may be operatively coupled to the RA lead 120, the LV lead 124, and the RV lead 130 (all three leads shown in FIG. 1) through the switch 174 to sample cardiac signals across any pair of desired electrodes.

The microcontroller 160 includes timing control module 161 to control the timing of the stimulation pacing pulses, including, but not limited to, pacing rate, atrio-ventricular delay, interatrial conduction delay, interventricular conduction delay, and/or intraventricular delay. The timing control module 161 can also keep track of the timing of refractory periods, blanking intervals, noise detection windows, evoked response detection windows, alert intervals, marker channel timing, etc., which is known in the art.

The microcontroller 160 further includes an arrhythmia detector 162 for operating the system 100 as an implantable cardioverter/defibrillator device. The detector 162 determines desirable times to administer various therapies. For example, the detector 162 may detect the occurrence of an arrhythmia and automatically control the application of an appropriate electrical shock therapy to the heart aimed at terminating the detected arrhythmia. To this end, the microcontroller 160 further controls a shocking circuit 173 by way of a control signal 179. The shocking circuit 173 generates shocking pulses that are applied to the heart of the patient through at least two shocking electrodes. The shocking pulses may be selected from the LA coil electrode 128, the RV coil electrode 136, and/or the SVC coil electrode 138 (all three electrodes shown in FIG. 1). The CAN 140 may act as an active electrode in combination with the RV coil electrode 136, or as part of a split electrical vector using the SVC coil electrode 138 or the LA coil electrode 128 (e.g., with the RV coil electrode 136 as a common electrode).

The microcontroller 160 may additionally include a morphology detector 164 and a multi-site left ventricular (MSLV) controller 165. The MSLV controller 165 controls multi-site LVEC pacing therapy, which can be performed in conjunction with CRT pacing. As an example, the MSLV controller 165 may control the pulse generator 172 to simultaneously deliver a pacing pulse over a select LVEC pacing vector. The LVEC pacing vector may extend between an RV electrode and a combination of LV electrodes. The LVEC pacing vector may also be referred to as a combination pacing vector as a combination of LV electrodes are used as a joint cathode. The arrhythmia detector 162, morphology detector 164, and/or MSLV controller 165 may be implemented in hardware as part of the microcontroller 160, or as software/firmware instructions programmed into the system 100 and executed on the microcontroller 160 during certain modes of operation.

A CRT controller 166 within the microcontroller 160 controls the actual delivery of CRT pacing pulses to synchronize the contractions of the right and left ventricles. The CRT controller 166 controls the number, timing, and output of the CRT pacing pulses delivered during each cardiac cycle, as well as over which pacing vectors the pacing pulses are to be delivered. The CRT controller 166 also selects the sensing channels over which the responses to the pulses are detected. The sensing channels or vectors are associated with corresponding pacing vectors. Immediately after pacing, the electrodes at the LV sensing sites that define the selected sensing channels monitor the LV tissue for a sensed activation event.

The microcontroller 160 further includes a local capture detection module 163. The capture detection module 163 may aid in acquisition, analysis, etc., of data streams relating to evoked responses sensed at various LV sensing sites along corresponding sensing channels. In particular, the capture detection module 163 may act to distinguish local capture versus non-capture versus undesired fusion of pacing pulses delivered along corresponding pacing vectors. The capture detection module 163 may communicate with the MSLV controller 165 and/or the CRT controller 166 to determine capture thresholds of individual pacing vectors associated with one or more LV sensing sites. The capture threshold may be used by the microcontroller 160 to determine the LVEC pacing site and the pacing vector at the LVEC pacing site along which to deliver LV pacing pulses, as described further below.

In an embodiment, the microcontroller 160 includes an arrival measurement (AM) module 167, a delay calculation (DC) module 168, and a site designation (SD) module 169. For example, when determining a preferred LVEC pacing site, as further described herein, the AM module 161 may be configured to measure arrival times of LV activation events for corresponding LV sensing sites. The arrival times each correspond to a conduction time from delivery of the pacing pulse until sensing of the corresponding LV activation event. The AM module 167 may include timer electronic circuitry to measure the arrival times.

The DC module 168 is configured to calculate site-to-site (STS) relative delays as differences between the arrival times associated with adjacent LV sensing sites, the STS relative delays representing STS arrival delays for corresponding combination of the adjacent LV sensing sites. For example, the DC module 168 may calculate a STS relative delay between any pair or any other combination of the adjacent LV sensing sites. In an embodiment, the DC module 168 may calculate the differences between an arrival time at each of the LV sensing sites and an arrival time at an adjacent LV sensing site. The DC module 168 may further calculate a local conduction velocity based on the STS relative delays and STS relative distances between the LV electrode corresponding to the adjacent LV sensing site. The calculating operation further comprises quantifying a spatiotemporal non-uniformity as the select degree of non-uniformity based on local conduction velocity. The microcontroller 160 may execute the programmable instruction to implement the DC module 168 to calculate the relative STS delays. Optionally, the DC module 168 may comprise electronic circuitry to calculate the STS relative delays. For example, the DC module 168 may perform this function in an out-of-clinic setting when the IMD 100 automatically tests to determine whether the current LVEC pacing site is still preferable, or if one or more other LVEC sites would be more preferable than the current LVEC pacing site.

The SD module 169 is configured to designate the first LVEC pacing site from which to deliver LVEC pacing pulses based on STS relative delays. The SD module 169 is configured to identify an LV electrode combination associated with at least one of the STS relative delays that satisfies selection criteria, where the LV electrode combination corresponds to a target tissue region exhibiting a select degree of non-uniformity as indicated by the corresponding STS relative delay. The SD module 169 designates the LV electrode combination as a first LVEC pacing site from which to deliver LV pacing pulses. For example, if an STS relative delay between LV electrodes M3 and P4 exceeds all other STS relative delays, then the SD module 169 would designate the electrodes M3 and P4 as the first LVEC pacing site. Once the SD module 169 designates the first LVEC pacing site, the pulse generator 172 is configured to deliver a pacing pulse or sequence from the first LVEC pacing site. Even if the pulse generator 172 is configured to deliver a pacing sequence from multiple LVEC pacing sites, a first LVEC pacing pulse in the sequence may be delivered from the first LVEC pacing site designated by the SD module 169. The selection criteria maybe based in part on a relation between the STS relative delays and a maximum arrival time difference among the LV electrodes on the lead. Optionally, the microcontroller 160 may execute the programmable instructions in memory 194 to implement the site designation module 169 to identify the LV electrode combination associated with one of the STS relative delays and to designate the LV electrode combination as the first LVEC pacing site.

The pulse generators 170, 172 deliver a pacing sequence from the LV electrode combination designated for the first LVEC pacing site. The pulse generators 170, 172 deliver a first LV pacing pulse in the pacing sequence from the LV electrode combination. As noted herein, the LV electrode combination includes an adjacent pair of LV electrodes. The pulse generators 170, 172 are coupled to the switch 174 that sets the adjacent pair of LV electrodes as cathodes when delivering the LV pacing pulse. Optionally, the pulse generators 170, 172 and switch 174, controlled by the site designation module 169 (or MSLV controller 165) designate adjacent at least first and second LV electrodes as cathodes to simultaneously deliver at least a first pacing pulse.

The SD module 169 may also be configured to designate an LVEC pacing site when none of the STS relative delays exceeds one another by a threshold. For example, when none of the STS relative delays exceeds one another by a threshold, the SD module 169 may retain a previously designated LVEC pacing site as unchanged from which to deliver LV pacing pulses. Optionally, the SD module 169 may designate an LVEC pacing site having a pacing vector with a lowest capture threshold as the first LVEC pacing site, due to energy conservation. In order to determine relative capture thresholds of pacing vectors, the SD module 169 may obtain a capture threshold of at least one pacing vector at each LV sensing site. Optionally, the SD module 169 may designate one or more pacing vectors that have a capture threshold above a predetermined value as non-pacing vectors. The non-pacing vectors are not to be used as pacing vectors at the first LVEC pacing site due to the energy expense necessary to achieve local capture.

Depending upon the implementation, the aforementioned components of the microcontroller 160 may be implemented in hardware as part of the microcontroller 160, or as software/firmware instructions programmed into the device and executed on the microcontroller 160 during certain modes of operation. In addition, the modules may be separate software modules or combined to permit a single module to perform multiple functions. For example, the AM module 167 and the DC module 168 may be combined into the same module. In addition, although shown as being components of the microcontroller 160, some or all of the components/modules described above may be implemented separately from the microcontroller 160 using application specific integrated circuits (ASICs) or the like.

The microcontroller 160 is further coupled to a memory 194 by a suitable data/address bus 196. The programmable operating parameters used by the microcontroller 160 are stored in the memory 194 and modified, as required, in order to customize the operation of IMD 100 to suit the needs of a particular patient. Such operating parameters define, for example, the amplitude or magnitude of the generated pacing pulses, wave shape, pulse duration, and/or vector (e.g., including electrode polarity) for the pacing pulses. Other pacing parameters may include base rate, rest rate, and/or circadian base rate. The memory 194 also may be utilized to store, at least temporarily, determined characteristics about one or more pacing vectors, such as local capture thresholds and the presence or absence of phrenic nerve stimulation (PNS), which is a potential side effect.

Optionally, the operating parameters of the implantable IMD 100 may be non-invasively programmed into the memory 194 through a telemetry circuit 101 in telemetric communication with an external programmer device 104 or a bedside monitor 102, such as a programmer, trans-telephonic transceiver, or a diagnostic system analyzer. The telemetry circuit 101 is activated by the microcontroller 160 through a control signal 106. The telemetry circuit 101 may allow IEGMs and status information relating to the operation of IMD 100 (contained in the microcontroller 160 or the memory 194) to be sent to the external device 102, and vice-versa, through an established communication link 103. An internal warning device 121 may be provided for generating perceptible warning signals to a patient and/or caregiver via vibration, voltage, or other methods.

IMD 100 further includes an accelerometer or other physiologic sensor 108. The physiologic sensor 108 is commonly referred to as a "rate-responsive" sensor because it may be used to adjust the pacing stimulation rate according to the exercise state (e.g., heart rate) of the patient. However, the physiological sensor 108 may further be used to detect changes in cardiac output, changes in the physiological condition of the heart, and/or diurnal changes in activity (e.g., detecting sleep and wake states and arousal from sleep). Accordingly, the microcontroller 160 may respond to such changes by adjusting the various pacing parameters (such as rate, interatrial delay, interventricular delay, etc.) at which the atrial and ventricular pulse generators 170 and 172 generate stimulation pulses. While shown as being included within IMD 100, it is to be understood that the physiologic sensor 108 may also be external to the IMD 100. Optionally, the physiologic sensor 108 may still be implanted within or carried by the patient. A common type of rate responsive sensor 108 is an activity sensor incorporating an accelerometer or a piezoelectric crystal, which is mounted within the housing/case 140 of IMD 100. Other types of physiologic sensors 108 are also known, such as sensors that sense the oxygen content of blood, respiration rate and/or minute ventilation, pH of blood, ventricular gradient, stroke volume, cardiac output, contractility, and the like.

The IMD 100 additionally includes a battery 110, which provides operating power to all of the circuits shown in FIG. 2. The makeup of the battery 110 may vary depending on the capabilities of IMD 100. If the system only provides low voltage therapy (e.g., for repetitive pacing pulses), a lithium iodine or lithium copper fluoride cell may be utilized. For a IMD that employs shocking therapy, the battery may be configured to be capable of operating at low current drains for long periods and then providing high-current pulses (for capacitor charging) when the patient requires a shock pulse. The battery 110 may also be configured to have a predictable discharge characteristic so that elective replacement time can be detected.

As further shown in FIG. 2, the IMD 100 has an impedance measuring circuit 112, which is enabled by the microcontroller 160 via a control signal 115. Uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 112 is coupled to the switch 174 so that any desired electrode may be used.

The above described implantable medical device 100 was described as an exemplary IMD. One of ordinary skill in the art would understand that one or more embodiments herein may be used with alternative types of implantable devices. Accordingly, embodiments should not be limited to using only the above described device 100.

Figure 3:
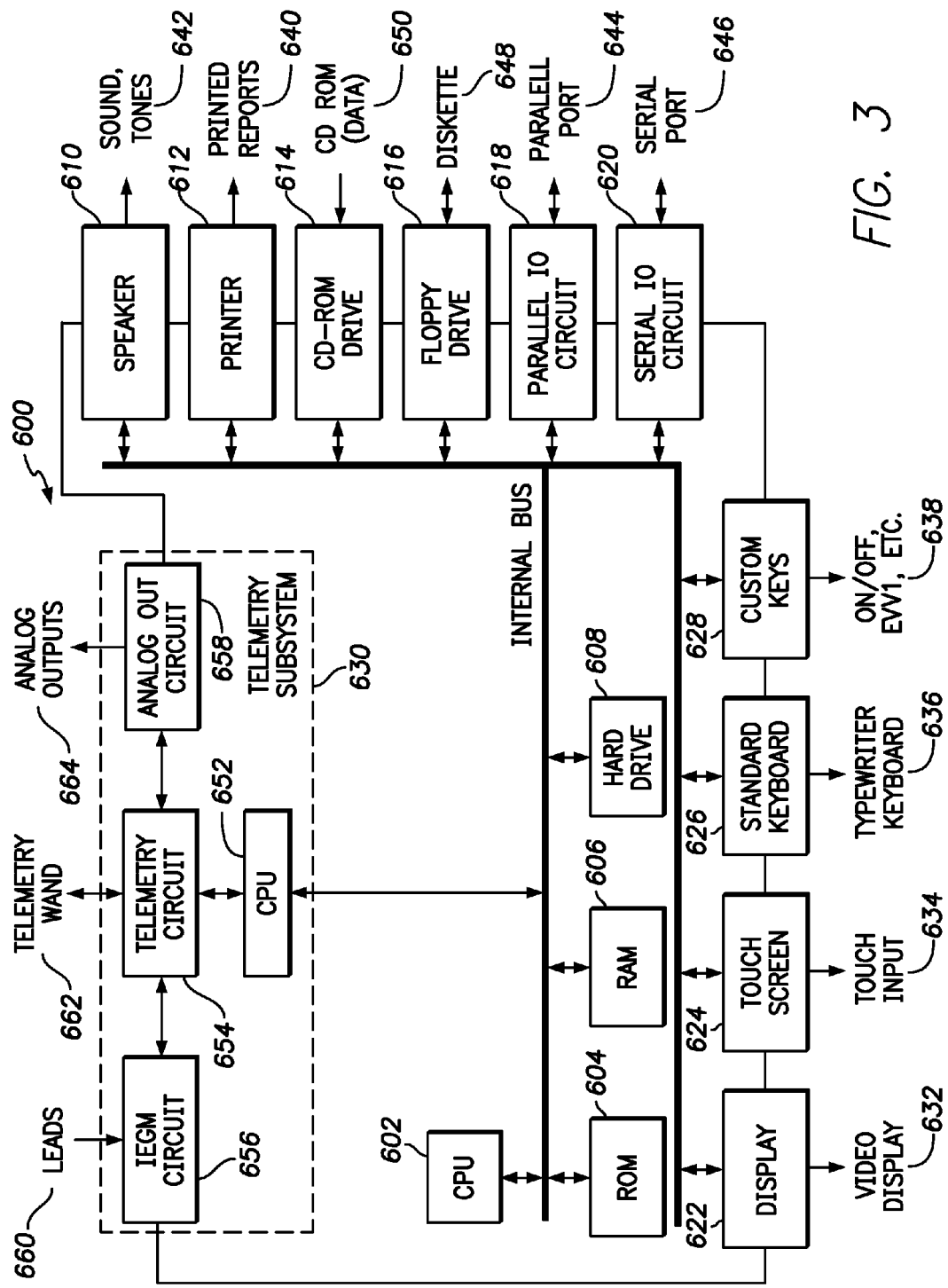
FIG. 3 illustrates a functional block diagram of an external device that is operated in accordance with the processes described herein.

FIG. 3 illustrates a functional block diagram of an external device 600 that is operated in accordance with the processes described herein and to interface with the implantable medical device 100 as shown in FIGS. 1 and 2 and described herein. The external device 600 may be the external programmer device 104 shown in FIG. 2. The external device 600 may take the form of a workstation, a portable computer, an IMD programmer, a PDA, a cell phone, and the like. The external device 600 includes an internal bus that connects/interfaces with a Central Processing Unit (CPU) 602, ROM 604, RAM 606, a hard drive 608, a speaker 610, a printer 612, a CD-ROM drive 614, a floppy drive 616, a parallel I/O circuit 618, a serial I/O circuit 620, a display 622, a touch screen 624, a standard keyboard 626, custom keys 628, and/or a telemetry subsystem 630. The internal bus is an address/data bus that transfers information between the various components described herein. The hard drive 608 may store operational programs as well as data, such as waveform templates, determinations on presence of PNS at various electrode locations, and/or capture thresholds for pacing vectors.

The CPU 602 includes a microprocessor, a micro-controller, and/or equivalent control circuitry, designed specifically to control interfacing with the external device 600 and with the IMD 100. The CPU 602 may include RAM or ROM memory, logic and timing circuitry, state machine circuitry, and/or I/O circuitry to interface with the IMD 100. The ROM 604, RAM 606 and/or hard drive 608 store program instructions that one executed by one or more processors (e.g., the CPU 602) to perform the operations described herein in connection with FIGS. 4A and 4B, as well as the operations of the MSLV controller 165, CRT controller 166, modules 161-164, and modules 167-169.

The display 622 may be connected to a video display 632. The display 622 displays various forms of information related to the processes described herein. The touch screen 624 may display graphic user information relating to the IMD 100. The touch screen 624 accepts a user's touch input 634 when selections are made. The keyboard 626 (e.g., a typewriter keyboard 636) allows a user to enter data to displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a flash memory stick. The CD-ROM drive 614 accepts CD ROMs 650. The CD-ROM drive 614 optionally may include a DVD port capable of reading and/or writing DVDs.

The telemetry subsystem 630 includes a central processing unit (CPU) 652 in electrical communication with a telemetry circuit 654, which communicates with both an IEGM circuit 656 and an analog out circuit 658. The IEGM circuit 656 may be connected to leads 660. The IEGM circuit 656 is also connected to the implantable leads 120, 124 and 130 (shown in FIG. 1) to receive and process IEGM cardiac signals. Optionally, the IEGM cardiac signals sensed by the leads 120, 124 and 130 may be collected by the IMD 100 and then wirelessly transmitted to the telemetry subsystem 630 input of the external device 600.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, 4G, satellite, as well as circuit and packet data protocols, and the like. Alternatively, a hard-wired connection may be used to connect the external device 600 to the IMD 100.

Figure 4A:
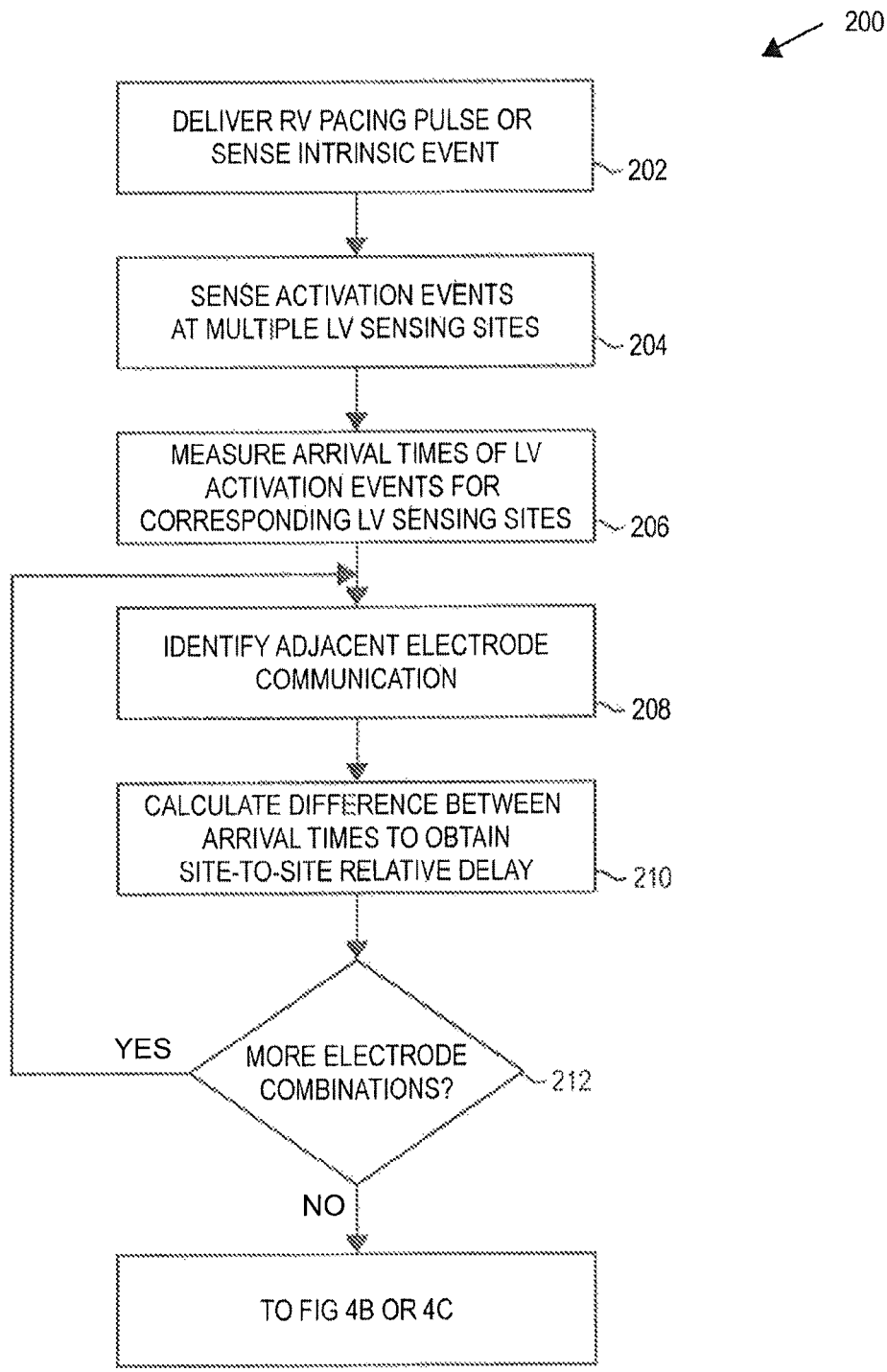
FIG. 4A is a flow chart for a process for determining site to site relative delays between LV sensing sites along a multi-pole lead in accordance with embodiments herein.

FIG. 4A is a flow chart for a process 200 for determining STS relative delays between LV sensing sites using a multi-pole lead according to embodiments herein. The process 200, for example, may employ structures or aspects of various embodiments (e.g., systems and/or methods) discussed herein. For example, the process 200 may be performed using the IMD 100 shown in FIGS. 1 and 2. Optionally, an external programmer, such as external device 600 shown in FIG. 3, may be used in conjunction with the IMD 100 to perform the process 200. The process 200 is described herein with reference to the IMD 100, although other devices may be used instead of or in addition to the IMD 100. In various embodiments, certain aspects of the process 200 may be omitted or added, certain aspects may be combined, certain aspects may be performed simultaneously, certain aspects may be performed concurrently, certain aspects may be split into multiple aspects, certain aspects may be performed in a different order, or certain aspects or series of aspects may be re-performed in an iterative fashion.

In various embodiments, some portions, aspects, and/or variations of the process 200 may be able to be used as one or more algorithms to direct hardware to perform operations described herein. For example, the process 200 may be implemented in an algorithm that controls the IMD 100 to automatically select, program, and/or reprogram at least one LVEC pacing site according to the operations described herein. The process 200 may be performed in a clinic under the supervision of a clinician and/or in an unsupervised out-of-clinic setting. For example, the process 200 may suggest an LVEC pacing cathode to the clinician at implant of the IMD 100 and during in-clinic follow-ups. For example, suggested LVEC pacing sites maybe be suggested using, e.g., display 622 (shown in FIG. 3) associated with programming device 600 and/or IMD 100. Out of the clinic, the process 200 may be performed to automatically reprogram the LVEC pacing cathode to a more preferred LVEC pacing site to produce an improved hemodynamic response to CRT.

At 202, an intrinsic ventricular event occurs or a reference pacing pulse is delivered from at least one RV or RA pacing site. The pacing pulse is generated by the pulse generator 170 and/or the pulse generator 172, depending on the reference pacing site selected. For example, the reference pacing site may be selected by the clinician or automatically by the microcontroller 160. As used herein, pacing site refers to the location of the cathode that is used to deliver a pacing pulse along a pacing vector. Example pacing pulses at an RV pacing site may be delivered at the RV tip electrode 132 or the RV ring electrode 134, along the pacing vectors RV tip 132 to RV coil 136 or RV ring 134 to RV coil 136, respectively. Optionally, the pacing vector may be unipolar between an RV cathode and the CAN 140. Example RA pacing sites may be at the atrial tip electrode 122 or the atrial ring electrode 123, along the pacing vectors from the respective electrodes 122, 123 to the SVC coil 138 or to the CAN 140. The pacing pulse may be delivered by the microcontroller 160 by sending a control signal 176, 178 to one or both pulse generators 170, 172 that identifies the pacing vector, the electrical output, the timing, and the like. The pulse generator 170 and/or 172 in response generates an electrical potential at one or both electrodes that define a selected pacing vector, resulting in a potential difference between the electrodes that induces a depolarization wave in the surrounding heart tissue.

While the process of FIG. 4A illustrates how to measure STS relative delays when a pacing pulse is delivered in the ventricles, optionally, the process of FIG. 4A may measure STS relative delays during intrinsic ventricular activation (e.g. during a patient's intrinsic rhythm, or atrial pacing).

At 204, LV activation events at multiple LV sensing sites are sensed. The LV activation events are generated in response to the pacing pulse or an intrinsic event. The LV activation events are detected responses to the propagating depolarization wave, and are detected along sensing vectors associated with corresponding LV sensing sites. As used herein, an LV sensing site refers to the location of an LV electrode that at least partially defines a sensing vector or channel over which the delivered pacing pulse is sensed. For example, the multiple LV sensing sites correspond to the locations of the LV electrodes, such as D1, M2, M3, and P4 of the quadripolar LV lead 124. In an embodiment, the IMD 100 senses along at least four sensing vectors, where each sensing vector utilizes a sensing cathode electrode in the left ventricle. The sensing vectors associated with the LV sensing sites may be unipolar vectors D1-CAN, M2-CAN, M3-CAN, and P4-CAN, where the CAN represents the anode electrode and D1, M2, M3 and P4 represent the cathode electrode. The pacing pulse is delivered at a RV pacing site and sensed at various LV sensing sites. This configuration may be referred to as RV pace-LV sense. Optionally, sensing vectors other than unipolar vectors may be used, such as D1-RV coil 136. In accordance with at least some embodiments, the sensing vectors are assigned to exclude LV electrodes as anodes and limit the LV electrodes to be cathodes.

In an embodiment, the LV activation events are sensed by at least one sensor. For example, the sensor may be the ventricular sensing circuit 184, which includes an amplifier. For example, sensed electrical activity (e.g., voltage and/or current) at each electrode in a sensing vector may be routed as signals through the electrode configuration switch 174 to the ventricular sensing circuit 184. The ventricular sensing circuit 184 may amplify, convert, and/or digitize the received signals before forwarding the signals to the microcontroller 160 for recordation and analysis of the data. Optionally, various other sensors and/or sensing circuits may be used to sense the LV activation events instead of or in addition to the ventricular sensing circuit 184.

At 206, arrival times of the LV activation events for corresponding LV sensing sites are measured (e.g., by the arrival measurement module 167 and/or CPU 602). The arrival times (e.g., conduction delays) each correspond to a conduction time from delivery of the pacing pulse until sensing of the corresponding LV activation event. For example, arrival times may be measured by recording the time (e.g. designated as time $T_O$) that a pacing pulse is delivered at an RV site, recording the times (e.g. designated as times $T_{D1}, T_{M2}, T_{M3}, T_{P4}$) of the LV activation events at each of the LV sensing sites, and subtracting the time of the pacing pulse from the times of the LV activation events (e.g., $T_O-T_{D1}$). Optionally, the arrival times may be measured using an internal timer (associated with each sensing site for each sensing circuit) by starting the timer when the pacing pulse is delivered and stopping the timer when each LV activation event occurs to determine the arrival time of each respective LV activation event. As an example, if it takes 60 ms after an RV pacing pulse for the sensor (e.g., sensing circuit 184) to detect an LV activation event at an LV sensing site, then the arrival time for that LV sensing site is 60 ms. The arrival times at the different LV sensing sites may vary due to the difference in locations of the LV electrodes relative to the cathode at the RV pacing site. Due to the different relative locations, the propagation wave may reach some LV sensing sites sooner than other sensing sites, resulting in a shorter arrival time.

The arrival times may be measured by the arrival measurement module 167 within the microcontroller 160. Optionally, the arrival times may be measured by the external programmer device 600. In such case, the IMD 100 may signal to the device 600 the time that a pacing pulse is delivered as well as the times for each of the LV activation events so the device 600 can determine the arrival times. For example, the device 600 may be a Merlin™ programmer (developed by St. Jude Medical, Inc.) with a freeze capture and calipers function capable of determining the time from the RV pacing marker to LV activation on each of the unipolar LV sensing vectors (e.g., D1-CAN, M2-CAN, M3-CAN, P4-CAN).

At 208, the microcontroller 160 and/or CPU 602 identifies adjacent electrode combinations available at the LV lead 124. For example, when the LV lead 124 includes the electrodes D1, M2, M3 and P4, the adjacent electrode combinations would include D1+M2, M2+M3 and M3+P4. As noted herein, an adjacent electrode combination may include more than two electrodes that are arranged successive with one another. For example, an adjacent electrode combination may represent D1+M2+M3, M2+M3+P4, and the like. Each adjacent electrode combination represents adjacent LV sensing sites for which the process may determine whether the local tissue exhibits heterogeneity electrical behavior or dyssynchrony.

At 210, the microcontroller 160 and/or CPU 602 calculates a difference between the arrival times for a select combination of the adjacent electrodes to obtain a site-to-site (STS) relative delay between the select combination of the adjacent LV sensing sites. For example, STS relative delay$_{D1,M2}$ for the electrode combination D1+M2 may be calculated by subtracting the arrival time associated with the LV sensing site at the D1 electrode from the arrival time associated with the LV sensing site at the M2 electrode. Therefore, if the arrival time at sensing site D1 is measured to be 80 ms, and the arrival time at sensing site M2 is 87 ms, the STS relative delay$_{D1, M2}$ would be the difference, 7 ms. The STS relative delays may be calculated by the delay calculation (DC) module 168 within the microcontroller 160, and/or the CPU 602.

At 212, the microcontroller 160 and/or CPU 602 determines whether additional electrode combinations exist, for which an STS relative delay should be determined. When additional electrode combinations exist, flow returns to 208. Otherwise, the flow advances to the operation at FIG. 4B or 4C.

Optionally, the external programmer device 600 may perform one or more of the operations described in connection with FIG. 4A, such as to calculate the STS relative delays for the various electrode combinations of the LV sensing sites. In an embodiment, STS relative delays may be calculated for every available combination of the LV sensing sites. That is, the arrival time at each LV sensing site is subtracted from the arrival time at every other adjacent LV sensing site. For example, for LV electrodes D1, M2, M3, and P4, STS relative delays may be computed for the combinations: D1+M2, M2+M3 and M3+P4, D1+M2+M3, M2+M3+P4. Note that these example combinations represent pairings of nearest neighbor electrodes, not vectors, so the order of the electrodes in each pair is irrelevant.

Optionally, when measuring the arrival times, the shortest arrival time from among the LV sensing sites may be determined. If the LV sensing site with the shortest or earliest arrival time is known, then only the differences between the arrival time at each of the LV sensing sites and the earliest arrival time need be calculated. Assuming, for example, that LV sensing site M3 is earliest with an arrival time of 67 ms, then the STS relative delays need only be calculated for the combinations D1–M3, M2–M3, and P4–M3. Therefore, if the earliest arrival time is known, fewer STS relative delays need to be calculated. In an embodiment, a clinician during implantation of the IMD 100 or during a follow-up may obtain STS relative delays for all of the available combinations, or for at least the combinations between the arrival times of the LV sensing sites and the earliest measured arrival time. That way, the clinician (or microcontroller 160) may analyze how all of the arrival times for each of the LV sensing sites compare in order to determine one or more preferred LVEC pacing sites.

When the patient is out of the clinic, LVEC pacing therapy from a previously-selected LVEC pacing site may be currently taking place. At a designated time, the IMD 100 may automatically perform the process 200 to determine whether the current LVEC pacing site is still preferred. For example, the IMD 100 may perform process 200 to test whether the previously-selected LVEC site is still a preferred LVEC pacing site that will provide the best available acute hemodynamic response, or whether reprogramming the IMD 100 to pace from a different LVEC site would provide an improved acute hemodynamic response. In such situation, only the STS relative delays between the arrival time at the current LVEC pacing site and the arrival times at the other LVEC pacing sites need be calculated. For example, if electrode M2 is the current LVEC pacing site, the combinations may be M2-D1, M2-M3, and M2-P4, and the pacing therapy will only be reprogrammed to deliver pacing from a different LVEC pacing site if another LVEC pacing site is preferable over the current site at the M2 electrode. Therefore, only the STS relative delays that compare the other LVEC pacing sites to the current LVEC pacing site are desirable. Optionally, STS relative delays may still be calculated for all available combinations of LVEC sensing sites, not just the combinations involving the current LVEC pacing site. The determination of whether one LVEC site would be preferable over another LVEC pacing site is discussed herein below.

Figure 5:
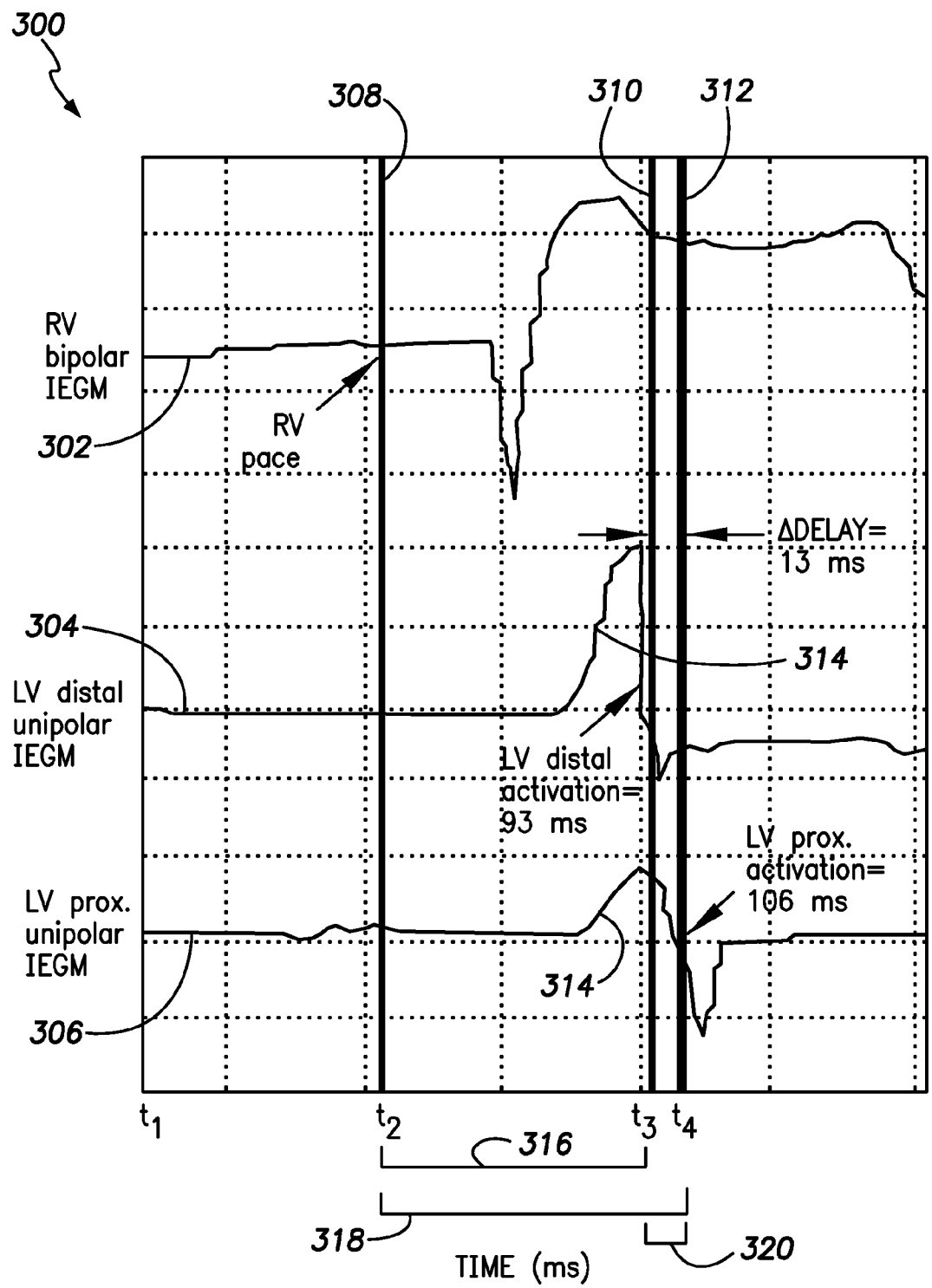
FIG. 5, a graph is displayed plotting multiple data streams measured in connection with different sensing sites.

Referring now to FIG. 5, a graph 300 is displayed plotting multiple data streams measured in connection with different sensing sites. The data streams may be displayed on the graph 300 as intracardiac electrogram (IEGM) waveforms representative of the electrical activity in ventricular tissue (measured in mV) over time (measured in ms). The graph 300 displays an IEGM waveform 302 associated with an RV electrode and two IEGM waveforms 304, 306 associated with an LV distal electrode and an adjacent LV electrode, respectively. For example, the RV electrode may be the RV tip 132 or RV ring 134, the LV distal electrode may be electrode D1 or M2, and the LV adjacent electrode may be P4 or M3. The three IEGM waveforms 302-306 may be representative of the electrical activity sensed along sensing vectors at least partially defined by the respective corresponding electrodes. For example, waveform 302 may represent activity sensed along the bipolar RV vector RV tip 132 to RV coil 136, while the waveforms 304, 306 may represent activity sensed along unipolar LV vectors from the respective LV electrodes to the CAN.

The graph 300 displays the waveforms 302-306 vertically separated in order to compare the shape of the waveforms 302-306 over time. It should be recognized that the waveforms 302-306 share a common time scale but not the same electrical activity scale, meaning that the vertical distance between one waveform from the other waveforms does not represent a difference in the measured mV. The graph 300 may be a screenshot of a display (e.g., display 622 shown in FIG. 3) associated with programmer device 600 and/or IMD 100. Alternatively, the graph 300 may not be displayed, and is included herein for illustrative purposes to explain the internal process operations of the programmer device 600 and/or IMD 100.

The graph 300 of FIG. 5 illustrates how arrival times of LV activation events may be measured at operation 206 of process 200 (shown in FIG. 4A) as well as how STS relative delays may be calculated at operation 208 of process 200 (of FIG. 4A). For example, each of the sensing vectors may begin sensing for electrical activity at time $t_1$. At time $t_2$, an RV pacing pulse is delivered at an RV pacing site, which is denoted on the graph 300 by an RV pace marker 308. As the depolarization wave propagates through the myocardial tissue, the activity sensed at the RV and LV sensing sites are recorded in the waveforms 302-306. For example, the wave is used for biventricular (BiV) pacing, as the pulse delivered in the right ventricle propagates to the left ventricle where it is sensed at the LV sensing sites. The LV distal electrode waveform 304 indicates the presence of an LV activation event at time $t_3$, while the LV adjacent electrode waveform 306 indicates an LV activation event afterwards at time $t_4$. The LV activation events for the LV distal electrode and the LV adjacent electrode are denoted by activation event markers 310 and 312, respectively.

As shown in graph 300, the activation event markers 310, 312 represent the midpoint of the negative slope of the R-wave 314, which represents intrinsic ventricular depolarization, or the maximum negative slope of the R-wave 314. Optionally, the markers 310, 312 may be located at other locations along the R-waves 314 of the waveforms 304, 306, as long as the location selected is the same for both waveforms 304, 306, for comparison purposes. For example, the markers 310, 312 optionally may be located at the starting point of the R-wave 314 (e.g., leftmost location with a positive amplitude), the midpoint of the positive slope of the R-wave 314, the point of maximum positive slope, the apex of the R-wave 314, the nadir or lowest point of the R-wave 314, and the like. Optionally, the markers 310, 312 may be positioned manually by a clinician using a user interface (e.g., touch input 634 and/or typewriter keyboard 636 of programmer device 600 shown in FIG. 3) to interact with the graph 300 on the display 622. Alternatively, markers 310, 312 may be positioned automatically, and the arrival times and STS relative delays calculated automatically, by the IMD 100 and/or external programmer device 600 without assistance from a clinician or another third party. As such, the graph 300 may be purely a read-only and non-interactive graphic.

Once the LV activation events 310, 312 are determined, the arrival times for each of the LV sensing sites are computed by measuring the time between the time of the RV pacing pulse 308 and the times of the activation events 310, 312. For example, the LV activation event 310 for the LV distal electrode occurs at time $t_3$, the RV pacing pulse 308 occurs at time $t_2$, so the arrival time 316 for the LV sensing site at the LV distal electrode is the difference between times $t_3$ and $t_2$. As shown in FIG. 5, that difference was measured to be 93 ms, which represents the arrival time 316 of the LV activation event 310 at the LV distal sensing site. Likewise, the arrival time 318 for the LV activation event 312 at the LV proximal sensing site is represented as the time difference between the event 312 at time $t_4$ and the pacing pulse at time $t_2$, which is measured to be 106 ms. Since the arrival times 316, 318 for respective LV distal and proximal sensing sites are known, the STS relative delay between these two sensing sites may be calculated as the difference between the two times 316, 318. For example, as shown in FIG. 5, the STS relative delay (e.g., $\Delta$delay) 320 for the combination of the LV distal sensing site and the LV proximal sensing site is 13 ms, calculated by subtracting 93 ms from 106 ms. The 13 ms delay 320 represents the time delay from time $t_3$ to time $t_4$.

Figure 4B:
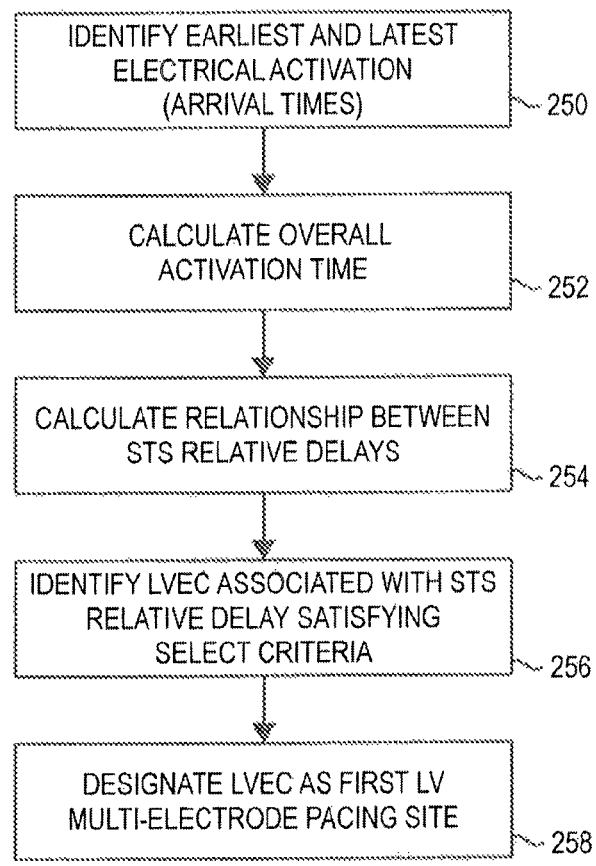
FIG. 4B illustrates a process for designating a first LVEC pacing site in accordance with embodiments herein.

FIG. 4B illustrate a process for designating a first LV multi-electrode pacing site in accordance with embodiments herein. The operations of FIG. 4B may be implemented by one or more of the structures and modules illustrated in FIGS. 2 and/or 3 and described in connection therewith.

The process of FIG. 4B may employ structures or aspects of various embodiments (e.g., systems and/or methods) discussed herein. For example, the process may be performed using the IMD 100 shown in FIGS. 1 and 2.

Optionally, an external programmer, such as external device 600 shown in FIG. 3, may be used in conjunction with the IMD 100 to perform the process of 4B. The process of 4B is described herein with reference to the IMD 100, although other devices may be used instead of or in addition to the IMD 100. In various embodiments, certain aspects of the process of 4B may be omitted or added, certain aspects may be combined, certain aspects may be performed simultaneously, certain aspects may be performed concurrently, certain aspects may be split into multiple aspects, certain aspects may be performed in a different order, or certain aspects or series of aspects may be re-performed in an iterative fashion. In various embodiments, some portions, aspects, and/or variations of the process of FIG. 4B may be able to be used as one or more algorithms to direct hardware to perform operations described herein. For example, the process may be implemented in an algorithm that controls the IMD 100 to automatically select, program, and/or reprogram at least one LVEC pacing site according to the operations described herein. The process may be performed in a clinic under the supervision of a clinician and/or in an unsupervised out-of-clinic setting. For example, the process may suggest an LVEC pacing cathode to the clinician at implant of the IMD 100 and during in-clinic follow-ups. Out of the clinic, the process 200 may be performed to automatically reprogram the LVEC pacing cathode to a more preferred LVEC pacing site to produce an improved hemodynamic response to CRT.

At 250, the microcontroller 160 and/or CPU 602 identify an earliest electrical activation time (arrival time) experienced by one of the LV electrodes. The delay calculation module 168 and/or CPU 602 also identify the latest electrical activation time (arrival time) experienced by another of the LV electrodes. As one example, the LV electrode P4 may sense an activation event first, relative to the other LV electrodes, and as such experience the earliest activation time. Depending upon a direction of propagation of an activation wavefront, the LV electrode D1 may sense an activation event last, relative to the other LV electrodes. Alternatively, when the activation wavefront propagates in a different direction, one of LV electrodes M2 or M3 may sense a first activation event, while one of LV electrodes D1 and P4 may sense a last activation event.

At 252, the microcontroller 160 and/or CPU 602 calculate an overall activation time interval representing the total time between first and last activation events sensed at the various LV electrodes (e.g., max(t)−min(t)). The overall activation time interval may correspond to a maximum activation time difference. Optionally, the overall activation time interval may be determined in other manners. For example, an activation event sensed by one or more of the LV electrodes may be declared to be an invalid event and as such disqualified from the calculation for the overall activation time interval. Invalid events may be based upon the morphology of the sensed event, as well as other characteristics.

At 254, the microcontroller 160 and/or CPU 602 calculate a relationship between the STS relative delays. For example, the calculation of the relationship may include calculating a ratio for each STS relative delay as a percentage of the overall activation time interval. For example, when the overall activation time interval equals 250 ms, and an STS relative delay (e.g. for the LV electrode combination P4–M3) equals 50 ms, the ratio associated with the LV electrode combination P4–M3 is ⅕ or 20% ($RD_{43}=(t_4-t_3)/[\max(t)-\min(t)]$). A ratio is calculated for each electrode combination and associated STS relative delay. While the present example utilizes percentage as a relationship, it is recognized that other mathematical relations may be used. For example, the relationship may represent a ratio between the STS relative delays of various electrode combinations (e.g., the ratio of the STS relative delay of P4–M3 versus the STS relative delay of M3–M2, the review of the STS relative delay of P4–M3 versus the STS relative delay of M2–D1, etc.). As another example, the relationship may represent a difference between the STS relative delays of various electrode combinations. The relationships are determined at 254 for each LV electrode combination of potential use for an LVEC pacing site.

At 256, the microcontroller 160 and/or CPU 602 identifies one of the STS relative delays that satisfies a selection criteria, as well as the corresponding LV electrode combination. Optionally, the selection criteria may correspond to a relation between the STS relative delays and the overall activation time interval. For example, the selection criteria may be based in part on a relation between the STS relative delays and a maximum arrival time difference among the LV electrodes. The maximum arrival time difference may represent the difference between an earliest arrival time sensed by the LV electrodes and a latest arrival time sensed by the LV electrodes. Optionally, the selection criteria may be based on the ratios/differences of the STS relative delays, such that the STS relative delay having the largest ratio/difference from the other STS relative delays satisfies the selection criteria. The LV electrode combination may include an adjacent pair of LV electrodes, where the method utilizes the adjacent pair of LV electrodes as cathodes when delivering the LV pacing pulses.

At 258, the microcontroller 160 and/or CPU 602 designate the LV electrode combination identified at 256 as the first LV multi-electrode pacing site, also referred to as the first LVEC pacing site. The LV electrode combination designated at 256 represents two or more LV electrodes to be used as cathodes when delivering at least a first pacing pulse. The first LVEC pacing site corresponds to two of a D1, M2, M3, or P4 electrode provided on the multi-pole LV lead. The designating operation may include designating adjacent at least the first and second LV electrodes as cathodes to simultaneously deliver at least a first pacing pulse. When a series of pacing pulses are to be delivered, at least the first pacing pulse in the series is delivered utilizing the two or more LV electrodes as cathodes, designated at 258. Optionally at 258 the process delivers a pacing sequence from the LV electrode combination designated for the first LVEC pacing site, wherein a first LV pacing pulse in the pacing sequence is delivered from the LV electrode combination. Optionally, at 258, the process may configure the first LVEC pacing site to be a cathode within a pacing vector, the pacing vector extending between the first LVEC pacing site and at least one of a CAN electrode, a right atrial electrode, and a right ventricular electrode.

Figure 4C:
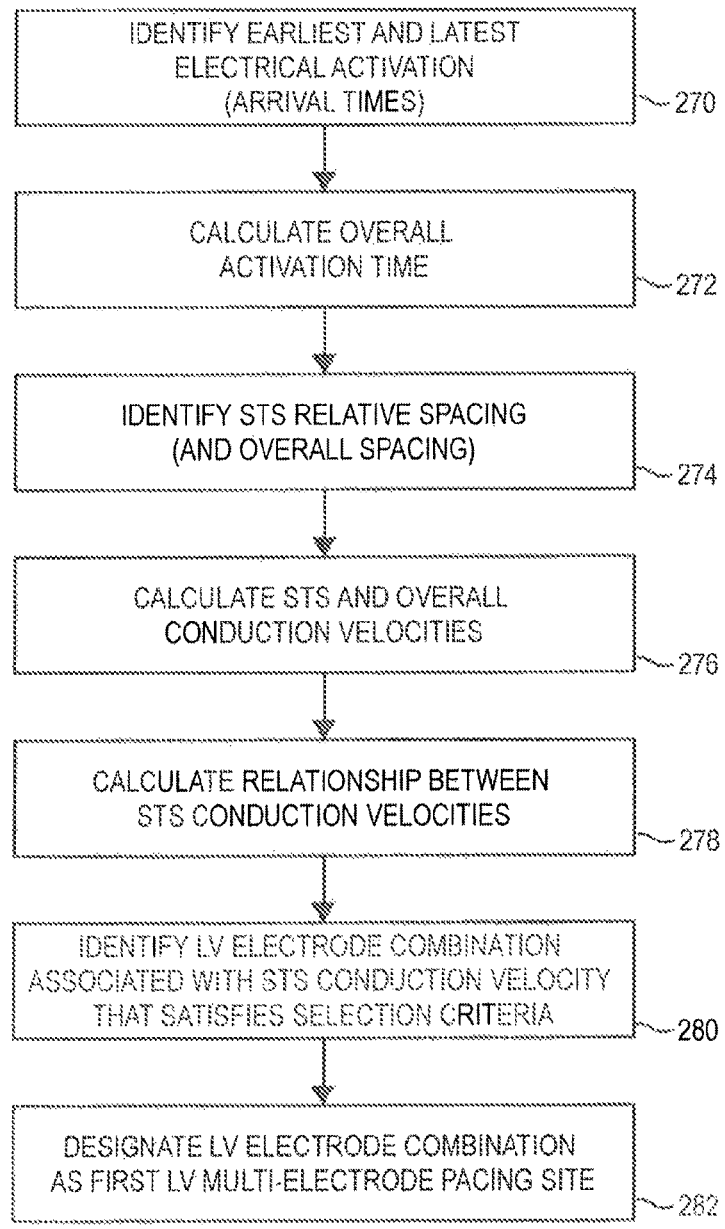
FIG. 4C illustrates an alternative process for designating a first LVEC pacing site in accordance with embodiments herein.

FIG. 4C illustrate a process for designating a first LV multi-electrode pacing site in accordance with alternative embodiments herein. The operations of FIG. 4C may be implemented by one or more of the structures and modules illustrated in FIGS. 2 and/or 3 and described in connection therewith. The process of FIG. 4C may employ structures or aspects of various embodiments (e.g., systems and/or methods) discussed herein. For example, the process may be performed using the IMD 100 shown in FIGS. 1 and 2. Optionally, an external programmer, such as external device 600 shown in FIG. 3, may be used in conjunction with the IMD 100 to perform the process of FIG. 4C. The process of FIG. 4C is described herein with reference to the IMD 100, although other devices may be used instead of or in addition to the IMD 100. In various embodiments, certain aspects of the process of FIG. 4C may be omitted or added, certain aspects may be combined, certain aspects may be performed simultaneously, certain aspects may be performed concurrently, certain aspects may be split into multiple aspects, certain aspects may be performed in a different order, or certain aspects or series of aspects may be re-performed in an iterative fashion. In various embodiments, some portions, aspects, and/or variations of the process of FIG. 4C may be able to be used as one or more algorithms to direct hardware to perform operations described herein. For example, the process may be implemented in an algorithm that controls the IMD 100 to automatically select, program, and/or reprogram at least one LVEC pacing site according to the operations described herein. The process may be performed in a clinic under the supervision of a clinician and/or in an unsupervised out-of-clinic setting. For example, the process may suggest an LVEC pacing cathode to the clinician at implant of the IMD 100 and during in-clinic follow-ups. Out of the clinic, the process 200 may be performed to automatically reprogram the LVEC pacing cathode to a more preferred LVEC pacing site to produce an improved hemodynamic response to CRT.

At 270, the microcontroller 160 and/or CPU 602 identify an earliest electrical activation time (arrival time) experienced by one of the LV electrodes. The microcontroller 160 and/or CPU 602 also identify the latest electrical activation time (arrival time) experienced by another of the LV electrodes. At 272, the microcontroller 160 and/or CPU 602 calculate an overall activation time interval representing the total time between first and last activation events sensed at the various LV electrodes. The overall activation time interval may correspond to a maximum activation time difference.

At 274, the microcontroller 160 and/or CPU 602 identify STS relative spacings between the various combinations of LV electrodes. For example, the STS relative spacings may correspond to the relative distances between centers of each pair of neighboring LV electrodes. As one example, the STS relative spacing between the centers of a pair of neighboring electrodes may represent an axial measurement (STS axial spacing) along a longitudinal length of the LV lead when the distal portion of the LV lead (in which the LV electrodes are positioned) is oriented in a generally straight manner. For example, when the distal portion of the LV lead is oriented along a linear axis, the spacing of the electrodes D1, M2, M3 and P4 from the distal end of the LV lead may be 5, 20, 30 and 50 mm, respectively. It is recognized that the spacing is simply one example of the spacing between LV electrodes and other spacings may be utilized. When STS axial spacings are to be used, the values may be pre-stored in memory and simply accessed during operation.

FIG. 6A illustrates examples of STS relative spacings for distal portions of an LV lead that may be shaped in accordance with embodiments herein. Within FIG. 6A, the distal portions 702, 704 and 706 may correspond to a common lead, but bent in different manners based upon the venous branch. The distal portions 702, 704 and 706 each include LV electrodes P4, M3, M2 and D1. The electrodes P4 and M3 have an STS axial spacing 716. The electrodes M3 and M2 have an STS axial spacing 718. The electrodes M2 and D1 have an STS axial spacing 720. The distal portion of the LV lead may be shaped in different manners based upon the venous branch in which the lead is placed. For example, the distal portion 706 may be positioned in a venous branch which maintains the distal portion in a relatively straight manner. Alternatively, the distal portion 704 may be positioned in a venous branch that slightly bends the distal portion. Alternatively, the distal portion 702 may position in a venous branch that substantially bends the lead, such as in an S-shape.

When the LV lead is shaped corresponding to the distal portion 706, the STS axial spacings 716-720 between the electrodes (P4, M3, M2 and D1) along the longitudinal axis of the lead generally may be used as the STS relative spacing (at 274 in FIG. 4C). However, when the LV lead is shaped, corresponding to the distal portion 702, the axial spacing between the electrodes (P4, M3, M2 and D1) does not necessarily correspond to the actual STS relative spacing. Instead, the electrodes M2 and D1 may have an STS relative spacing 710 that is less than the axial spacing 720. Similarly, the electrodes P4 and M3 may have an STS relative spacing 714 that is less than the axial spacing 716.

When the axial spacings 716-720 do not accurately reflect the STS relative spacing, the STS relative spacing may be identified at 274 in various manners. For example, a fluoroscopic image may be acquired during pre-implant planning, during implantation or thereafter to estimate the level or degree to which the distal portion is (or will be) bent into an S shape or other non-linear shape. As one example, different degrees of bend may be assigned numeric or descriptive ranks. For example, the degree of bend illustrated in FIG. 6A corresponding to the distal portions 702-706 may be rated as a 2, 1 or 0 bend degree, respectively. The fluoroscopy may be used to identify the amount of bend, from which a user may enter a bend rating (e.g. 0, 1 or 2; small, medium, large, M3–M2 large; P4–M3 slight, etc.). The microcontroller 160 and/or CPU 602 may utilize the predetermined STS axial spacings 716-720, in combination with the user entered bend rating to obtain an STS relative spacing. For example, when a bend rating of 1 is designated, the STS axial spacings 716 and 720 may be reduced by a predetermined percentage (e.g., 25%), while the STS axial spacing 718 is used as the STS relative spacing. Alternatively, a bend rating of 2 may indicate that the STS axial spacings 716 and 720 should be reduced by 50% to obtain the corresponding STS relative spacings. Additionally or alternatively, another bend rating may indicate that the STS axial spacing 718 should be reduced, while the STS axial spacings 716 and 720 should be used without reduction as the STS relative spacings at 274.

Returning to FIG. 4C, at 276, the microcontroller 160 and/or CPU 602 calculate STS conduction velocities based on the STS relative spacings and the STS relative delays (obtained at 210 in FIG. 4A). For example, attention is directed to FIG. 6B. FIG. 6B illustrates an example of calculations of STS conduction velocities between various LV electrode combinations resulting from a waveform propagating from the distal and to the proximal end of the LV lead. In FIG. 6B, arrows 750 represent a direction of electrical wavefront propagation, where the wavefront arrives at electrode D1 at time $T_1$, electrode M2 at time $T_2$, electrode M3 at time $T_3$, and electrode P4 at time $T_4$. The STS conduction velocity is calculated by dividing the STS relative spacing ($d_{43}$) by the difference in the arrival times at each electrode. For example, the STS conduction velocity associated with the LV electrode combination P4–M3 may be quantified by the equation: $CV_{43}=d_{43}/(t_4-t_3)$. At 276, the STS conduction velocity is calculated for each LV electrode combination: $CV_{43}$ (for P4–M3), $CV_{32}$ (for M3–M2), and $CV_{21}$ (for M2–D1).

At 278, the microcontroller 160 and/or CPU 602 calculate a relation between the STS conduction velocities. For example, the relationship may correspond to a ratio of each conduction velocity to an overall conduction velocity between P4 and D1. Additionally or alternatively, the relationship may correspond to a ratio between various combinations of STS conduction velocities. Additionally or alternatively, the relationship may correspond to a difference between various combinations of STS conduction velocities.

At 280, the microcontroller 160 and/or CPU 602 identifies the LV electrode combination associated with the STS conduction velocity that satisfies a selection criteria of interest. The selection criteria may correspond to the relationship between the STS conduction velocities and the overall conduction velocity. The selection criteria may seek to maximize the relationship. For example, the process may identify the STS conduction velocity that represents the largest percentage of the overall conduction velocity, when compared to other STS conduction velocities. The LV electrode combination selection criteria may be based in part on a relation between the STS conduction velocity and a maximum conduction velocity among the LV electrodes. Optionally, the selection criteria may be based on the ratios/differences of the STS conduction velocities.

At 282, the microcontroller 160 and/or CPU 602 designate the LV electrode combination identified at 280 as the first LV multi-electrode pacing site. The process of FIG. 4C determines distances between adjacent LV electrodes on the multi-pole LV lead and identifies the LV electrode combination that satisfies the selection criteria based in part on the distances between adjacent LV electrodes.

In accordance with the processes of FIGS. 4B and 4C, the LV electrode combination that has a characteristic of interest, such as a largest STS relative delay or STS conduction velocity, is designated as a first LVEC pacing site from which to deliver LV pacing pulses. The first LVEC pacing site may correspond to two or more of the D1, M2, M3, or P4 electrodes provided on the multi-pole LV lead. Once the first LVEC pacing is identified, it may be automatically set or presented as a suggestion to a user of an external programmer. By designating the first pacing LV site, the IMD 100 may automatically program or reprogram to deliver future pacing sequences from the first LVEC pacing site. Additionally, or alternatively, the IMD 100 may be configured to provide a recommendation to a physician. This recommendation may be useful in the clinic setting, where the physician/clinician is able to set the pacing parameters on-site based in part on the recommendations from the IMD 100.

Although one or more currently preferable LVEC pacing sites may be programmed through performing the process described herein, during the course of CRT the electrical activation pattern may change as LV remodeling occurs. As a result, a previously-designated LVEC pacing site may no longer be preferable over one or more other LV sites. To keep the pacing at a preferred site out-of-clinic, the IMD 100 may be programmed to automatically perform the RV pacing to LV sensing measurements at a frequency selected by the clinician. The frequency may be every day, every week, every two weeks, and the like.

It is to be understood that the above description is intended to be illustrative, and not restrictive. For example, the above-described embodiments (and/or aspects thereof) may be used in combination with each other. In addition, many modifications may be made to adapt a particular situation or material to the subject matter of an embodiment described herein without departing from scope of the teachings herein. While the dimensions, types of materials and coatings described herein are intended to define parameters of one or more embodiments, they are by no means limiting and are exemplary embodiments. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for selecting a left ventricular (LV) multi-electrode (LVME) pacing site for an implantable medical device equipped for cardiac stimulus pacing using a multi-pole LV lead, the method comprising:
   sensing LV activation events at multiple LV sensing sites, where the activation events are generated in response to intrinsic ventricular events or delivery of a pacing pulse;
   measuring arrival times of the LV activation events for the corresponding LV sensing sites, wherein the arrival times each correspond to a conduction time from the intrinsic ventricular events or the delivery of the pacing pulse until sensing of the corresponding LV activation event;
   calculating site-to-site (STS) relative delays as differences between the arrival times associated with adjacent LV sensing sites, the STS relative delays representing STS arrival delays for corresponding combinations of the adjacent LV sensing sites;
   calculating a degree of non-uniformity based on the STS relative delays;
   identifying an LV electrode combination associated with at least one of the STS relative delays that satisfies selection criteria, the LV electrode combination corresponding to a target tissue region exhibiting a select degree of non-uniformity; and
   designating the LV electrode combination as a first left ventricular electrode combination (LVEC) pacing site from which to deliver LV pacing pulses; and
   delivering a LV pacing pulse from the first LVEC pacing site.

2. The method of claim 1, wherein the selection criteria is based in part on a relation between the STS relative delays and a maximum arrival time difference among the LV electrodes on the lead.

3. The method of claim 2, wherein the maximum arrival time difference represents the difference between an earliest arrival time sensed by the LV electrodes and a latest arrival time sensed by the LV electrodes.

4. The method of claim 1, further comprising delivering a pacing sequence from the LV electrode combination designated for the first LVEC pacing site, wherein a first LV pacing pulse in the pacing sequence is delivered from the LV electrode combination.

5. The method of claim 1, wherein the LV electrode combination includes an adjacent pair of LV electrodes, the method further comprising utilizing the adjacent pair of LV electrodes as cathodes when delivering the LV pacing pulses.

6. The method of claim 1, wherein the designating operation includes designating adjacent at least first and second LV electrodes as cathodes to simultaneously deliver at least a first pacing pulse.

7. The method of claim 1, wherein the calculating operation further comprises quantifying a spatiotemporal non-uniformity as the select degree of non-uniformity based on local conduction velocity.

8. The method of claim 1, wherein the calculating operation further comprises calculating a local conduction velocity based on the STS relative delays and STS relative distances between the LV electrode corresponding to the adjacent LV sensing sites.

9. The method of claim 1, further comprising configuring the first LVEC pacing site to be a cathode within a pacing vector, the pacing vector extending between the first LVEC pacing site and at least one of a CAN electrode, a right atrial electrode, and a right ventricular electrode.

10. The method of claim 1, wherein the first LVEC pacing site corresponds to two of a D1, M2, M3, or P4 electrode provided on the multi-pole LV lead.

11. The method of claim 1, further comprising determining distances between adjacent LV electrodes on the multi-pole LV lead, the identifying operation identifying the LV electrode combination that satisfies the selection criteria based in part on the distances between adjacent LV electrodes.

12. An implantable medical device equipped for cardiac stimulus pacing using a multi-pole left ventricular (LV) lead, the device comprising:
  a sensor configured to sense LV activation events at multiple LV sensing sites, where the activation events are generated in response to an intrinsic ventricular event or a delivery of a pacing pulse;
  an arrival measurement (AM) module configured to measure arrival times of the LV activation events for the corresponding LV sensing sites, wherein the arrival times each correspond to a conduction time from the intrinsic ventricular event or the delivery of the pacing pulse until sensing of the corresponding LV activation event;
  a delay calculation (DC) module configured to calculate:
    site-to-site (STS) relative delays as differences between the arrival times associated with adjacent LV sensing sites, the STS relative delays representing STS arrival delays for corresponding combinations of the adjacent LV sensing sites, and
    a degree of non-uniformity based on the STS relative delays; and
  a site designation (SD) module configured to identifying an LV electrode combination associated with at least one of the STS relative delays that satisfies a selection criteria, the LV electrode combination corresponding to a target tissue region exhibiting a select degree of non-uniformity, the SD module designating the LV electrode combination as a first left ventricular electrode combination (LVEC) pacing site from which to deliver LV pacing pulses.

13. The device of claim 12, wherein the selection criteria is based in part on a relation between the STS relative delays and a maximum arrival time difference among the LV electrodes on the lead.

14. The device of claim 12, further comprising a pulse generator to deliver a pacing sequence from the LV electrode combination designated for the first LVEC pacing site, the pulse generator to deliver a first LV pacing pulse in the pacing sequence from the LV electrode combination.

15. The device of claim 12, wherein the LV electrode combination includes an adjacent pair of LV electrodes, the device further comprising a pulse generator coupled to a switch that sets the adjacent pair of LV electrodes as cathodes when delivering the LV pacing pulses.

16. The device of claim 12, further comprising a pulse generator and switch, controlled by the site designation module to designate adjacent at least first and second LV electrodes as cathodes to simultaneously deliver at least a first pacing pulse.

17. The device of claim 12, further comprising a microcontroller and memory storing programmable instructions, the microcontroller executing the programmable instructions to implement the DC module to calculate the relative STS delays.

18. The device of claim 12, further comprising a microcontroller and memory storing programmable instructions, the microcontroller executing the programmable instructions to implement the site designation module to identify the LV electrode combination associated with one of the STS relative delays and to designate the LV electrode combination as the first LVEC pacing site.

19. The device of claim 12, wherein the AM module includes timer electronic circuitry to measure the arrival times, and the DC module comprising electronic circuitry to calculate the STS relative delays.

20. A system for cardiac stimulus pacing using a multi-pole left ventricular (LV) lead, the system comprising:
  memory to store arrival times of LV activation events for corresponding LV sensing sites, the LV activation events occurring at multiple LV sensing sites, wherein the activation events are generated in response to an intrinsic ventricular event or a delivery of a pacing pulse and wherein the arrival times each correspond to a conduction time from the intrinsic ventricular event or the delivery of a pacing pulse until sensing of the corresponding LV activation event;
  one or more processors coupled to the memory, wherein the memory further stores program instructions, wherein the program instructions are executable by the one or more processors to:
    calculate site-to-site (STS) relative delays as differences between the arrival times associated with adjacent LV sensing sites, the STS relative delays representing STS arrival delays for corresponding combinations of the adjacent LV sensing sites;
    calculate a degree of non-uniformity based on the STS relative delays;
    identify an LV electrode combination associated with at least one of the STS relative delays that satisfies a selection criteria, the LV electrode combination corresponding to a target tissue region exhibiting a select degree of non-uniformity; and
    designate the LV electrode combination as a first left ventricular electrode combination (LVEC) pacing site from which to deliver LV pacing pulses.

* * * * *